(12) United States Patent
Jun et al.

(10) Patent No.: US 8,197,903 B2
(45) Date of Patent: Jun. 12, 2012

(54) SURFACE MODIFIED ORGANIC INORGANIC HYBRID GLASS, PROTECTING GROUP INDUCED ALCOHOL OR ITS DERIVATIVE AND PRODUCING METHOD THEREOF

(75) Inventors: Chul-Ho Jun, Seoul (KR); Hyo-Seon Kim, Seoul (KR); Jung-Woo Park, Busan (KR)

(73) Assignee: Industry-Academic Cooperation Foundation Yonsei University, Seoul (KR)

( * ) Notice: Subject to any disclaimer, the term of this patent is extended or adjusted under 35 U.S.C. 154(b) by 683 days.

(21) Appl. No.: 12/226,445

(22) PCT Filed: Apr. 18, 2007

(86) PCT No.: PCT/KR2007/001886
§ 371 (c)(1),
(2), (4) Date: Apr. 3, 2009

(87) PCT Pub. No.: WO2007/120014
PCT Pub. Date: Oct. 25, 2007

(65) Prior Publication Data
US 2009/0274910 A1    Nov. 5, 2009

(30) Foreign Application Priority Data

Apr. 19, 2006  (KR) .................. 10-2006-0035282
Mar. 29, 2007  (KR) .................. 10-2007-0030673

(51) Int. Cl.
    *B05D 5/00*     (2006.01)
(52) U.S. Cl. .................................... 427/387; 427/389.7
(58) Field of Classification Search .................. None
    See application file for complete search history.

(56) References Cited

U.S. PATENT DOCUMENTS

| 4,851,150 | A | 7/1989 | Hench et al. |
| 5,371,262 | A | 12/1994 | Arkles |
| 5,420,323 | A * | 5/1995 | Jung et al. ............... 556/415 |
| 6,335,380 | B1 * | 1/2002 | Wilhelm et al. ............ 522/83 |
| 2002/0173670 | A1 * | 11/2002 | Arkles et al. ............. 556/465 |

FOREIGN PATENT DOCUMENTS

| WO | WO 92/22557 | A1 | 12/1992 |
| WO | WO 99/54412 | A1 | 10/1999 |
| WO | WO 2004/026943 | A1 | 4/2004 |
| WO | WO 2005/000943 | A1 | 1/2005 |

* cited by examiner

*Primary Examiner* — Erma Cameron
(74) *Attorney, Agent, or Firm* — Reinhart Boerner Van Deuren P.C.

(57) ABSTRACT

Disclosed are a protected alcohol or derivative thereof, a surface-modified organic-inorganic hybrid glass, and preparation methods thereof. More specifically, disclosed are a protected alcohol or derivative thereof and a surface-modified organic-inorganic hybrid glass, which are prepared by allowing a silane compound, having vinyl or a vinyl derivative, to react with an alcohol or derivative thereof or with an organic-inorganic hybrid glass, in the presence of an acid catalyst, a transition metal catalyst and an organic solvent, so as to introduce an organic group thereto even at room temperature, as well as preparation methods thereof. The disclosed invention allows a functional group to be effectively introduced into alcohol or a derivative thereof or into an organic-inorganic hybrid glass, not only high temperatures but also room temperature, and thus is highly effective in introducing compounds having a thermally sensitive functional group, for example, natural compounds or proteins. Also, the invention makes it possible to introduce various organic groups and to separate and purify organic macromolecule-bonded organosilane compounds using a silica gel column so as to effectively introduce large organic functional groups to inorganic materials. Accordingly, the invention is highly useful in the chemical industry.

11 Claims, 6 Drawing Sheets before treatment (left) and after treatment by Piranha solution (right)

SURFACE MODIFIED ORGANIC INORGANIC HYBRID GLASS, PROTECTING GROUP INDUCED ALCOHOL OR ITS DERIVATIVE AND PRODUCING METHOD THEREOF

CROSS-REFERENCE TO RELATED PATENT APPLICATIONS

This patent application is the National Stage of International Application No. PCT/KR2007/001886, filed Apr. 18, 2007, which published as WO 2007/120014, that claims the benefit of Korean Application No. 2007-0030673, filed Mar. 29, 2007 and Korean Application No. 2006-0035282, filed Apr. 19, 2006, the entire teachings and disclosures of which are incorporated herein by reference thereto.

TECHNICAL FIELD

The present invention relates to a protected alcohol or derivative thereof, a surface-modified organic-inorganic hybrid glass, and preparation methods thereof. More specifically, it relates to a protected alcohol or derivative thereof and a surface-modified organic-inorganic hybrid glass, which are prepared by allowing a silane compound, having vinyl or a vinyl derivative, to react with an alcohol or derivative thereof or with an organic-inorganic hybrid glass, in the presence of an acid catalyst, a transition metal catalyst and an organic solvent, so as to introduce an organic group thereto even at room temperature, as well as preparation methods thereof.

BACKGROUND ART

The O-silylation of alcohol is very important in organic synthesis. The reason is that, because the proton of alcohol reacts with a nucleophilic reagent in organic synthesis, the hydroxyl group of alcohol should be replaced by a protective group in order to block this reaction, and silylation of the hydroxylic group of alcohol can block this reaction, and is thus useful for the protection of alcohol. Because of this advantage, many O-silylation reactions have been studied and developed. However, most of the O-silylation reactions have a problem in that they should be used only in water-free conditions because they employ chlorosilane, hydrosilane and the like, which are highly reactive and are sensitive to water and the like. Also, because a stoichiometric amount of tertiary amine should be used as a proton acceptor, an amount of ammonium salt more than a stoichiometric amount is produced after the silylation reaction, and the removal thereof becomes a great problem.

Moreover, it is important in developing organic/inorganic hybrids to tightly link an organic compound to a solid surface, and the use of covalent bonding for such linkage is considered to be the most reliable method for surface modification.

A typical example is covalent bonding between solid silica, as a solid surface, and an organic compound, in which a silicon atom present on the surface of silica forms a Si—O—Si bond with the silicon atom of an organic silicon compound. Specifically, a Si—OH group on the silica surface reacts with the organic silicon compound, which has a leaving group such as a halide, alkoxy or an amino group on the silicon atom thereof, so as to form a Si—O—Si covalent bond.

In a sol-gel synthesis method, which is most widely known as an organic-inorganic hybrid synthesis method, trialkoxysilane is used to form a siloxane network through hydrolysis and condensation, thus immobilizing a functional group. This method has shortcomings in that it is difficult to introduce organic macromolecules, because alkoxysilane is sensitive to water, making it impossible to separate alkoxysilane through column chromatography, and when a functional group is located inside the network, it will be lost. Also, there is a shortcoming in that it is difficult to introduce bioactive molecules, such as natural compounds and proteins, due to the pH environment of a hydrolysis process which is a necessary process of the sol-gel method. As an alternative thereto, there is a grafting method of linking compounds directly to a solid support. This overcomes the shortcomings of the sol-gel method, but has problems in that it has a low loading rate in practical use and in that it is not easy to control functional groups.

To solve such shortcomings, a method including the use of an allylsilane organic compound, which is relatively stable in water, was recently developed, but it has a problem in that it requires high-temperature reflux to conduct the reaction, and thus it is difficult to apply to organic silicon compounds containing thermally sensitive organic groups.

DISCLOSURE

Technical Problem

The present invention has been made in order to solve the above-described problems occurring in the prior art, and it is an object of the present invention to provide a surface-modified organic-inorganic hybrid material which is obtained by dissolving a silane compound, having vinyl or a vinyl derivative, in an organic solvent, and allowing the silane compound solution to react with an organic-inorganic hybrid material in the presence of an acid catalyst and a transition metal catalyst so as to introduce an organic group into the organic-inorganic hybrid material even at room temperature.

Another object of the present invention is to provide a protected alcohol or derivative thereof, which are obtained by dissolving a silane compound, having vinyl or a vinyl derivative, in an organic solvent, and allowing the silane compound solution to react with an alcohol or derivative thereof in the presence of an acid catalyst and a transition metal catalyst so as to O-silylate the alcohol or derivative thereof.

Technical Solution

To achieve the above objects, according to one aspect of the present invention, there is provided a protected alcohol or derivative thereof, which are obtained by allowing a silane compound represented by Formula 1, having vinyl or a vinyl derivative, to react with an alcohol or derivative thereof, in the presence of a transition metal catalyst, an acid catalyst and an organic solvent, so as to O-silylate the alcohol or derivative thereof.

[Formula 1]

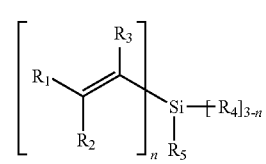

wherein $R_1$ to $R_4$ are each independently optionally substituted H or an optionally substituted alkyl group, $R_5$ is at least one selected from the group consisting of an optionally substituted alkyl or cycloalkyl group, an optionally substituted aromatic or heteroaromatic group, and optionally substituted halogen, azide, amine, ketone, ether, amide, ester, triazole and isocyanate groups, and n is an integer from 1 to 3.

Preferably, in Formula 1 above, $R_1$ to $R_4$ are each independently optionally substituted H or an optionally substituted $C_1$-$C_{30}$ alkyl group, and $R_5$ is at least one selected from the group consisting of an optionally substituted $C_1$-$C_{30}$ alkyl group, an optionally substituted $C_1$-$C_{30}$ cycloalkyl group, an optionally substituted $C_1$-$C_{30}$ aromatic or $C_1$-$C_{30}$ heteroaromatic ring compound, halogen, azide, amine, ketone, ether, amide, ester, triazole and isocyanate. The above reaction can be carried out at a temperature of 0-150°, and preferably 0-45°. As the transition metal catalyst, rhodium or iridium is preferably used, and as the acid, at least one selected from the group consisting of Bronsted acids, such as HCl, HBr and HI, is preferably used. As the organic solvent, at least one selected from the group consisting of aromatic and aliphatic solvents, such as toluene, benzene, methylene chloride, chloroform, dimethylacetamide (DMA) and $CCl_4$, is preferably used.

According to a second aspect of the present invention, there is provided a surface-modified organic-inorganic hybrid glass, which is obtained by allowing a silane compound represented by Formula 1, having vinyl or a vinyl derivative, to react with an organic-inorganic hybrid glass, in the presence of a transition metal catalyst, an acid catalyst and an organic solvent, so as to modify the surface of the organic-inorganic hybrid glass:

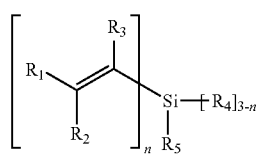

[Formula 1]

wherein $R_1$ to $R_4$ are each independently optionally substituted H or an optionally substituted alkyl group, $R_5$ is at least one selected from the group consisting of an optionally substituted alkyl or cycloalkyl group, an optionally substituted aromatic or heteroaromatic group, and optionally substituted halogen, azide, amine, ketone, ether, amide, ester, triazole and isocyanate groups, and n is an integer from 1 to 3.

Preferably, in Formula 1 above, $R_1$ to $R_4$ are each independently optionally substituted H or an optionally substituted $C_1$-$C_{30}$ alkyl group, and $R_5$ is at least one selected from the group consisting of an optionally substituted $C_1$-$C_{30}$ alkyl group, an optionally substituted $C_1$-$C_{30}$ cycloalkyl group, an optionally substituted $C_1$-$C_{30}$ aromatic or $C_1$-$C_{30}$ heteroaromatic ring compound, halogen, azide, amine, ketone, ether, amide, ester, triazole and isocyanate.

The organic-inorganic hybrid glass is solid silica or ITO glass. As the solid silica, amorphous silica or porous silica is preferably used. The reaction can preferably be carried out at a temperature ranging from 0 to 45°. As the transition metal catalyst, rhodium or iridium is preferably used. As the acid, at least one selected from the group consisting of HCl, HBr and HI is preferably used. As the organic solvent, at least one selected from the group consisting of toluene, benzene, methylene chloride, chloroform, THF and dimethylacetamide (DMA) is preferably used. The alkyl group in the definition of $R_5$ is preferably a propyl group. The radical $R_5$ can preferably be introduced with an organic group. The organic group that can be introduced is preferably at least one selected from the group consisting of amino acids, proteins, chiral compounds and natural compounds, but there is no particular limitation on the kind thereof, as long as it can modify the surface of the organic-inorganic hybrid glass. Preferably, the organic group can be introduced into the radical $R_5$ of the silane compound before or after the reaction between the organic-inorganic hybrid glass and the silane compound represented by Formula 1, having vinyl or a vinyl derivative.

As the silane compound, having vinyl or a vinyl group and represented by Formula 1, it is preferable to use 3-chloropropyldimethylvinylsliane, 3-chloropropylmethyldivinylsilane, or 3-chloropropyltrivinylsilane.

According to a third aspect of the present invention, there is provided a surface-modified organic-inorganic hybrid glass which is obtained by allowing a silane compound represented by Formula 1, having vinyl or a vinyl derivative, to react with an organic-inorganic hybrid glass, in the presence of rhodium (III) and an organic solvent, so as to modify the surface of the organic-inorganic hybrid glass:

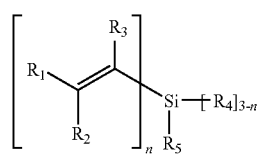

[Formula 1]

wherein $R_1$ to $R_4$ are each independently optionally substituted H or an optionally substituted $C_1$-$C_{30}$ alkyl group, $R_5$ is at least one selected from the group consisting of an optionally substituted $C_1$-$C_{30}$ alkyl group, an optionally substituted $C_1$-$C_{30}$ cycloalkyl group, an optionally substituted $C_1$-$C_{30}$ aromatic or $C_1$-$C_{30}$ heteroaromatic ring compound, halogen, azide, amine, ketone, ether, amide, ester, triazole and isocyanate, and n is an integer from 1 to 3.

According to a fourth aspect of the present invention, there is provided a method for modifying the surface of an organic-inorganic hybrid glass, the method comprising the steps of: 1) purifying a silane compound represented by Formula 1 below, having vinyl or a vinyl derivative; and 2) mixing an organic-inorganic hybrid glass with the purified silane compound, a transition metal catalyst, an acid catalyst and an organic solvent:

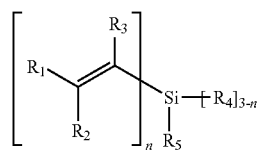

[Formula 1]

wherein $R_1$ to $R_4$ are each independently optionally substituted H or an optionally substituted alkyl group, $R_5$ is at least one selected from the group consisting of an optionally substituted alkyl or cycloalkyl group, an optionally substituted aromatic or heteroaromatic group, and optionally substituted halogen, azide, amine, ketone, ether, amide, ester, triazole and isocyanate groups, and n is an integer from 1 to 3.

Preferably, in Formula 1 above, $R_1$ to $R_4$ are each independently optionally substituted H or an optionally substituted $C_1$-$C_{30}$ alkyl group, and $R_5$ is at least one selected from the group consisting of an optionally substituted $C_1$-$C_{30}$ alkyl group, an optionally substituted $C_1$-$C_{30}$ cycloalkyl group, an optionally substituted $C_1$-$C_{30}$ aromatic or $C_1$-$C_{30}$ heteroaromatic ring compound, halogen, azide, amine, ketone, ether, amide, ester, triazole and isocyanate. The organic-inorganic hybrid glass is preferably solid silica or ITO glass. The purification of step 1) can preferably be carried out using column chromatography. The step 2) can be carried out at a temperature of 0-150°, and preferably 0-45°. As the transition metal catalyst, rhodium or iridium is preferably used, and as the acid, at least one selected from the group consisting of Bronsted acids, such as HCl, HBr and HI, is preferably used. As the organic solvent, at least one selected from the group consisting of toluene, benzene, methylene chloride, chloroform and dimethylacetamide (DMA) is preferably used. The surface modification method according to the present invention may preferably further comprise, after the step 2), a step of stirring the mixture for a period ranging from 5 minutes to 24 hours. Also, the method of the present invention may preferably further comprise, before the step 1) or after the step 2), a step of introducing an organic group into the radical $R_5$ of the silane compound. The organic group that is introduced into the radical $R_5$ may preferably be at least one selected from the group consisting of amino acids, proteins, chiral compounds and natural compounds.

The terms used herein will now be briefly described.

Unless stated otherwise, the term "optionally substituted" is meant to include the cases in which the groups in question may or may not be substituted with various substituents, including the case in which the groups are substituted with one or more substituents individually and independently selected from the group consisting of alkyl, cycloalkyl (including bicycloalkyl and tricycloalkyl), perhaloalkyl, aryl, heteroaryl, heteroalicyclic, hydroxy, alkoxy, azide, amine, ketone, ether, amide ester, triazole, isocyanate, arylalkyloxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, pyrrolidinone, pyrrolidine, piperidine, piperazine, morpholine, amine, amino (including mono- and di-substituted amino groups), and the protected derivatives thereof. In some cases, the substituents may also be optionally substituted.

The term "aromatic" refers to an aromatic group which has at least one ring having a conjugated pi electron system, and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "heteroaromatic" refers to an aromatic group including at least one heterocyclic ring. The term "alkyl" refers to an aliphatic hydrocarbon group. The alkyl moiety may be a "saturated alkyl", which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

As used herein, the substituent "R" appearing by itself and without a number designation refers to a substituent selected from the group consisting of optionally substituted alkyl, optionally substituted cycloalkyl, optionally substituted aryl, optionally substituted heteroaryl (bonded through a ring carbon) and optionally substituted heteroalicyclic (bonded through a ring carbon). The "O-carboxy" group refers to a RC(=O)O— group, wherein R is as defined herein. The "C-carboxy" group refers to a —C(=O)OR group, wherein R is as defined herein. The "acetyl" group refers to a —C(=O)CH$_3$ group. The "trihalomethanesulfonyl" group refers to a Z$_3$CS(=O)$_2$— group, wherein Z is a halogen. The "cyano" group refers to a —CN group. The "isocyanato" group refers to a —NCO group. The "thiocyanato" group refers to a —CNS group. The "isothiocyanato" group refers to a —NCS group. The "sulfinyl" refers to a —S(=O)—R group, wherein R is as defined herein. The "S-sulfonamido" group refers to a —S(=O)$_2$NR group, wherein R is as defined herein. The "N-sulfonamido" group refers to an RS(=O)$_2$NH— group, wherein R is as defined herein. The "trihalomethanesulfonamido" group refers to a Z$_3$CS(=O)$_2$NR— group, wherein Z and R are as defined herein. The "O-carbamyl" group refers to an —OC(=O)—NR group, with R as defined herein. The "N-carbamyl" group refers to an ROC(=O)NH— group, with R as defined herein. The "O-thiocarbamyl" group refers to an —OC(=S)—NR group, with R as defined herein. The "N-thiocarbamyl" group refers to an ROC(=S)NH— group, with R being as defined above. The "C-amido" group refers to a —C(=O)—NR$_2$ group, with R as defined above. The "N-amido" group refers to an RC(=O)NH— group, with R as defined above. The term "perhaloalkyl" refers to an alkyl group where some of the hydrogen atoms are replaced by halogen atoms. Other terms have the same meanings as generally understood in the art to which the present invention pertains.

Advantageous Effects

The present invention provides methods of using a silane compound, having vinyl or a vinyl derivative, to introduce a protective group into an alcohol or derivative thereof and to introduce an organic compound into an organic-inorganic hybrid glass. In these methods, a transition metal catalyst and an acid catalyst are used to increase reaction activity such that the alcohol can be effectively silylated even at room temperature. Also, the organic compound can be effectively introduced into solid silica or ITO glass, and thus the present invention is highly effective in introducing a natural compound or a thermally sensitive organic group into the solid silica or ITO glass. Furthermore, in the present invention, a process for pre-treating organic-inorganic hybrid glass is not required, and the reaction between the silane compound, having vinyl or a vinyl derivative, and the organic-inorganic hybrid glass, can be performed after an organic functional group is introduced into the silane compound. Accordingly, the present invention gives a high reaction yield and is highly useful in the chemical industry.

BEST MODE

Figure 1:
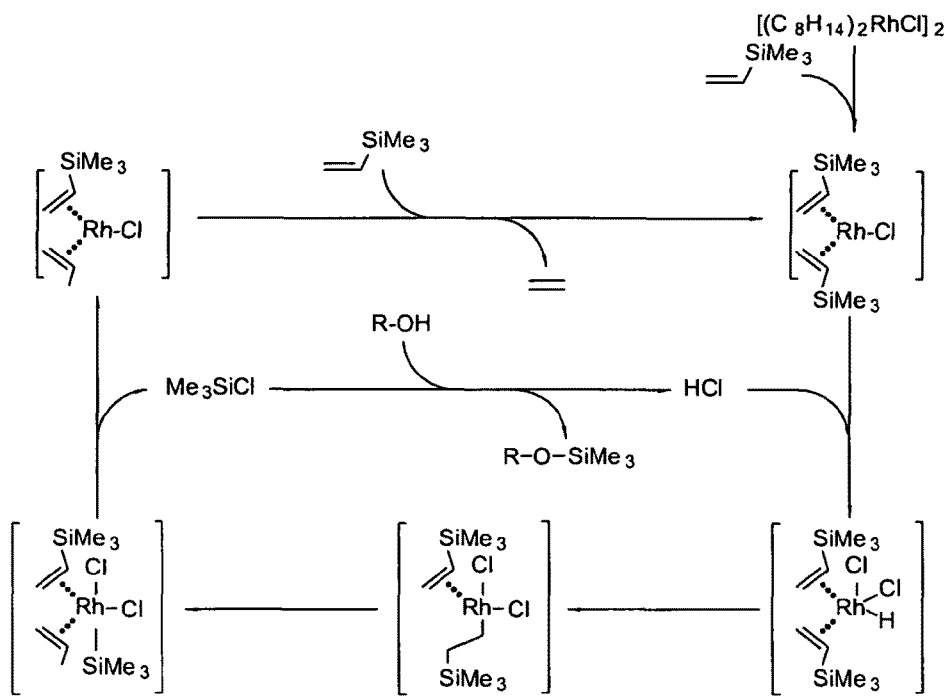
FIG. 1 shows a reaction mechanism for the O-silylation of alcohol with vinylsilane in the presence of a transition metal catalyst and an acid catalyst.

Hereinafter, the present invention will be described in further detail.

The O-silylation of alcohol is very important in organic synthesis. The reason is that, because the proton of alcohol reacts with a nucleophilic reagent in organic synthesis, the hydroxyl group of alcohol should be replaced by a protective group in order to block this reaction, and silylation of the hydroxylic group of alcohol can block this reaction, and thus is useful for the protection of alcohol. Because of this advantage, many O-silylation reactions have been studied and developed. However, most of the O-silylation reactions have a problem in that they should be used only in water-free conditions, because they employ chlorosilane, hydrosilane and the like, which are highly reactive and are sensitive to water and the like. Also, because a stoichiometric amount of tertiary amine should be used as a proton acceptor, an amount of ammonium salt more than a stoichiometric amount is produced after the silylation reaction, and the removal thereof becomes a great problem.

However, the O-silylation of alcohol according to the present invention has advantages in that it can be effectively performed even at room temperature using small amounts of a transition metal catalyst and an acid catalyst, and it is easy to remove by-products, because ethylene gas is produced as a by-product after the reaction.

Specifically, according to a first aspect of the present invention, there is provided a protected alcohol or derivative thereof which is synthesized by allowing a silane compound represented by Formula 1 below, having vinyl or a vinyl derivative, to react with alcohol or derivative thereof, in the presence of a transition metal catalyst, an acid catalyst and an organic solvent:

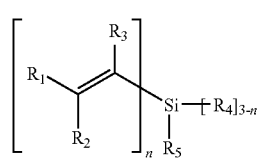

[Formula 1]

wherein $R_1$ to $R_4$ are each independently optionally substituted H or an optionally substituted alkyl group, $R_5$ is at least one selected from the group consisting of an optionally substituted alkyl or cycloalkyl group, an optionally substituted aromatic or heteroaromatic group, and optionally substituted halogen, azide, amine, ketone, ether, amide, ester, triazole and isocyanate groups, and n is an integer from 1 to 3.

Preferably, in Formula 1 above, R1 to R4 are each independently optionally substituted H or an optionally substituted $C_1$-$C_{30}$ alkyl group, and $R_5$ is at least one selected from the group consisting of an optionally substituted $C_1$-$C_{30}$ alkyl group, an optionally substituted $C_1$-$C_{30}$ cycloalkyl group, an optionally substituted $C_1$-$C_{30}$ aromatic or $C_1$-$C_{30}$ heteroaromatic ring compound, halogen, azide, amine, ketone, ether, amide, ester, triazole and isocyanate.

There is no limitation on the kind of alcohol or derivative thereof that can be used in the present invention, and primary alcohol, secondary alcohol and tertiary alcohol can all be used in the present invention. Also, as the silane compound having vinyl or a vinyl derivative, it is possible to use all compounds in which a silicon atom is substituted with 1-3 vinyl atoms, as shown in Formula 1 above. A preferred silane compound is trimethylvinylsilane, which is the most efficient. The protected alcohol or derivative thereof according to the present invention is characterized in that they are obtained by introducing a protective group into a highly reactive alcohol or a derivative thereof in various organic reactions. In the protected alcohol or derivative thereof according to the present invention, an organic group does not need to be introduced into the radical $R_5$ in Formula 1, but if necessary, various functional groups may be introduced.

Meanwhile, a mechanism for forming the protected alcohol or derivative thereof according to the present invention is shown in FIG. 1. As shown in FIG. 1, a transition metal catalyst and a silane compound having vinyl or a vinyl derivative react with each other to produce bis(trimethylvinylsilane). Then, HCl reacts with the bis(trimethylvinylsilane) rhodium to produce hydride, which is subjected to a metal-hydride insertion reaction to produce a rhodium-ethylsilyl complex. At this time, the silyl group moves due to a beta-silyl removal reaction and forms chlorotrimethylsilane with the chloride ions remaining after the formation of the rhodium-silyl complex. Then, it reacts with alcohol or an alcohol derivative to form a silylated compound, and the produced HCl continues to be used in a catalyst recycling process.

Meanwhile, the protected alcohol or derivative thereof may be deprotected through a general deprotection method after completion of the desired organic reaction. Specifically, it can be easily deprotected by adding an acid thereto, and then stirring or heating the mixture.

In order to perform the reaction for the formation of the protected alcohol or derivative thereof according to the present invention, both the transition metal catalyst and the acid catalyst should be added. As the transition metal catalyst, rhodium or iridium is preferably used in the present invention, but there is no limitation on the kind of transition metal catalyst. As the acid catalyst, at least one selected from the group consisting of Bronsted acids, such as HCl, HBr and HI, is preferably used in the present invention, but there is no particular limitation on the kind of acid catalyst. As the organic solvent, polar or non-polar solvents may all be used in the present invention, but toluene, benzene, methylene chloride, chloroform, THF and dimethylacetamide (DMA) are preferably used alone, or in a mixture of two or more thereof.

According to a second aspect of the present invention, there is provided a surface-modified organic-inorganic hybrid glass which is obtained by allowing a silane compound represented by Formula 1 below, having vinyl or a vinyl derivative, to react with an organic-inorganic hybrid glass, in the presence of a transition metal catalyst, an acid catalyst and an organic solvent, so as to modify the surface of the organic-inorganic hybrid glass:

[Formula 1]

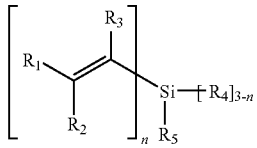

wherein $R_1$ to $R_4$ are each independently optionally substituted H or an optionally substituted alkyl group, $R_5$ is at least one selected from the group consisting of an optionally substituted alkyl or cycloalkyl group, an optionally substituted aromatic or heteroaromatic group, and optionally substituted halogen, azide, amine, ketone, ether, amide, ester, triazole and isocyanate groups, and n is an integer from 1 to 3.

Preferably, in Formula 1 above, $R_1$ to $R_4$ are each independently optionally substituted H, or an optionally substituted $C_1$-$C_{30}$ alkyl group, and $R_5$ is at least one selected from the group consisting of an optionally substituted $C_1$-$C_{30}$ alkyl, an optionally substituted $C_1$-$C_{30}$ cycloalkyl group, an optionally substituted $C_1$-$C_{30}$ aromatic or $C_1$-$C_{30}$ heteroaromatic ring compound, halogen, azide, amine, ketone, ether, amide, ester, triazole and isocyanate.

An organic-inorganic hybrid glass, which can be used in the present invention, is solid silica or ITO glass. As the solid silica, it is preferable to use amorphous silica or porous silica, which provide high efficiency, but there is no limitation on the kind of solid silica. As the ITO glass, conventional glass can be used in the present invention. Also, as the silane compound having vinyl or a vinyl derivative, it is possible to use all compounds in which a silicon atom is substituted with 1-3 vinyl atoms, as shown in Formula 1 above. A preferred silane compound is trimethylvinylsilane, which is the most efficient.

Meanwhile, in comparison with the above-described protected alcohol or derivative thereof, the surface-modified organic-inorganic hybrid glass according to the second aspect of the present invention is characterized in that a hydroxyl group on the surface of the organic-inorganic hybrid glass is modified with an organic compound having a functional group. Accordingly, as the functional group ($R_5$) of the silane compound, having vinyl or a vinyl derivative, any functional group can be used as long as it can introduce various organic groups through a series of chemical reactions (e.g., $S_N1$ and $S_N1$ reactions, click chemistry, Staudinger ligation, etc.). Preferably, in Formula 1, $R_1$ to $R_4$ are each independently optionally substituted H or an optionally substituted alkyl group, and $R_5$ is at least one selected from the group consisting of an optionally substituted alkyl or cycloalkyl group, an optionally substituted aromatic or heteroaromatic group, and optionally substituted halogen, azide, amine, ketone, ether, amide, ester, triazole and isocyanate groups. More preferably, $R_1$ to $R_4$ are each independently optionally substituted H or an optionally substituted $C_1$-$C_{30}$ alkyl group, and $R_5$ is at least one selected from the group consisting of an optionally substituted $C_1$-$C_{30}$ alkyl group, an optionally substituted $C_1$-$C_{30}$ cycloalkyl group, an optionally substituted $C_1$-$C_{30}$ aromatic or $C_1$-$C_{30}$ heteroaromatic ring compound, halogen, azide, amine, ketone, ether, amide, ester, triazole and isocyanate. Still more preferably, the alkyl group is a propyl group. The propyl group preferably comprises a functional group in view of reactivity and production cost.

Thus, the present invention aims to introduce various organic groups into the organic-inorganic hybrid by substituting the above-described functional groups with the organic groups. That is, the present invention aims to modify the surface of the organic-inorganic hybrid glass by introducing a variety of desired organic groups into the organic-inorganic hybrid glass through a suitable organic reaction. Particularly, because the method of the present invention can be conducted at room temperature, it is useful for introducing thermally unstable natural compounds or proteins, polymer compounds such as amino acids, or difficult-to-separate and difficult-to-purify chiral compounds. Furthermore, said $R_5$ group can be suitably selected depending on the kind of organic group that is introduced therein, and can be introduced with the organic group through organic reactions, such as single-step organic reactions or multiple-step organic reactions.

Meanwhile, the organic group to be introduced according to the present invention can be first introduced into the silane compound, having vinyl or a vinyl derivative, and can then be allowed to react with the organic-inorganic hybrid glass. Alternatively, the organic group can also be finally introduced into the organic-inorganic hybrid glass after allowing the organic-inorganic hybrid glass to react with the silane compound, having vinyl or a vinyl derivative. In other words, according to the present invention, the $R_5$ group of the silane compound, having vinyl or a vinyl derivative, is first introduced into the desired organic group, and the silane compound is then subjected to a purification process, such as column chromatography, and is finally allowed to react with the organic-inorganic hybrid glass. Alternatively, the silane compound, having vinyl or a vinyl derivative, is first allowed to react with the organic-inorganic hybrid glass, and then the desired organic group is introduced into the $R_5$ group.

Unlike the prior synthesis method, in which the reaction is carried out by reflux at high temperature in a toluene solvent, in the present invention, the reaction is carried out using the acid catalyst and the transition metal catalyst simultaneously. Particularly, the silane compound, having vinyl or a vinyl derivative, which is used in the present invention, can be stably used even in water and hydrolysis conditions, and can be separated and purified through column chromatography.

Also, the silane compound, having vinyl or a vinyl derivative, is activated in the presence of the transition metal catalyst and the acid catalyst such that it reacts with the Si—OH group of silica even at room temperature. Thus, it has an advantage in that it can be conveniently used even in the presence of thermally sensitive organic compounds or functional groups. In particular, it can be introduced into amorphous silica or mesoporous silica. Also, it can be used to modify the surface of ITO glass for use in the electronic industry or sensor applications, and thus can be widely applied in solid surface modification reactions and the like.

Meanwhile, in order to carry out the reaction for providing the surface-modified organic/inorganic hybrid glass according to the present invention, the transition metal catalyst and the acid catalyst should all be added.

As the transition metal catalyst for use in the present invention, it is preferable to use rhodium or iridium, but there is no particular limitation on the kind of transition metal catalyst.

As the acid catalyst, at least one selected from the group consisting of Bronsted acids, such as HCl, HBr and HI, is preferably used in the present invention, but there is no particular limitation on the kind of the acid catalyst.

As the organic solvent, polar or non-polar solvents may all be used in the present invention, but toluene, benzene, methylene chloride, chloroform, THF and dimethylacetamide (DMA) are preferably used, either alone or in a mixture of two or more thereof.

Meanwhile, the mechanism for modifying the surface of the organic-inorganic hybrid glass is carried out in a way that is very similar to the case of the above-described protected alcohol or derivative thereof. First, the transition metal catalyst reacts with the silane compound having vinyl or a vinyl derivative, to thus produce bis(trimethylvinylsilane). Then, HCl reacts with the bis(trimethylvinylsilane)rhodium to produce hydride, which is then subjected to a metal-hydride insertion reaction to produce a rhodium-ethylsilyl complex. At this time, the silyl group moves due to a beta-silyl removal reaction and forms chlorotrimethylsilane, with the chloride ions remaining after formation of the rhodium-silyl complex. Then, it reacts with alcohol or an alcohol derivative to form a silylated compound, and HCl, which is a by-product remaining after the reaction, continues to be used in a catalyst recycling process.

The reaction temperature in the present invention is not specifically limited, and the reaction can be carried out at high yield even at high temperatures. Preferably, the reaction can be actively carried out at 0-150°, and more preferably, it can be carried out even at 0-45°, without requiring a reflux or heating process. Accordingly, because the present invention uses the transition metal catalyst and the acid catalyst, it is very effective in increasing the reaction yield even at room temperature and in introducing a thermally sensitive organic group into the organic-inorganic hybrid glass. Thus, the present invention has the advantages of making a reaction process simple and of reducing production cost.

Accordingly, unlike the prior method of modifying the organic-inorganic hybrid glass using alkoxysilane or chlorosilane, the silane compound having vinyl or a vinyl derivative, which is used in the present invention, can be purified through column chromatography, because it does not react with the organic-inorganic hybrid glass at room temperature. Even in the case of vinylsilanes having organic compounds bonded thereto, which have a large molecular weight so as to make fractional distillation impossible, they can be purified through column chromatography. They can introduce various organic groups into the organic-inorganic hybrid glass, because they are activated by the transition metal catalyst and the acid catalyst even at room temperature, and react with the organic-inorganic hybrid glass.

According to a third aspect of the present invention, there is provided a surface-modified organic-inorganic hybrid glass which is obtained by allowing a silane compound represented by Formula 1 below, having vinyl or a vinyl derivative, to react with an organic-inorganic hybrid glass, in the presence of rhodium (III) and an organic solvent, so as to modify the surface of the organic-inorganic hybrid glass:

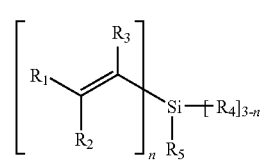

[Formula 1]

wherein $R_1$ to $R_4$ are each independently optionally substituted H or an optionally substituted $C_1$-$C_{30}$ alkyl group, $R_5$ is at least one selected from the group consisting of an optionally substituted $C_1$-$C_{30}$ alkyl group, an optionally substituted $C_1$-$C_{30}$ cycloalkyl group, an optionally substituted $C_1$-$C_{30}$ aromatic or $C_1$-$C_{30}$ heteroaromatic ring compound, halogen, azide, amine, ketone, ether, amide, ester, triazole and isocyanate, and n is an integer from 1 to 3.

The surface-modified organic-inorganic hybrid glass according to the third aspect is characterized in that the reaction for preparing it can be carried out only using rhodium (III) without adding any acid catalyst. This is believed to be because rhodium (III) is reduced by alcohol and vinylsilane to produce rhodium (I) and HCl, which act as catalysts, and thus the reaction is effectively carried out even at room temperature.

The surface-modified organic-inorganic hybrid glass according to the third aspect is prepared in the same manner as the second aspect, except that no acid catalyst is added.

According to a fourth aspect of the present invention, there is provided a method for modifying the surface of an organic-inorganic hybrid glass, the method comprising the steps of: 1) purifying a silane compound represented by Formula 1 below, having vinyl or a vinyl derivative; and 2) mixing an organic-inorganic hybrid glass with the purified silane compound, an acid, and an organic solvent:

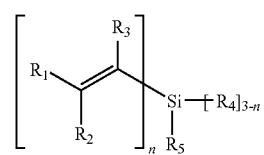

[Formula 1]

wherein $R_1$ to $R_4$ is H or a linear or branched $C_1$-$C_{30}$ alkyl group, $R_5$ is a linear or branched $C_1$-$C_{18}$ alkyl group, a linear or branched $C_1$-$C_{30}$ aliphatic unsaturated hydrocarbon, a $C_1$-$C_{30}$ ring compound, a $C_1$-$C_{30}$ aromatic ring compound, or a linear or branched $C_1$-$C_{18}$ alkyl group or linear or branched $C_1$-$C_{18}$ aliphatic unsaturated hydrocarbon containing at least one functional group selected from the group consisting of halogen, azide, amine, ketone, ether, amide, ester, triazole and isocyanate, and n is an integer from 1 to 3.

The purification step 1) can be performed using a reaction suitable for obtaining the desired silane compound, having vinyl or a vinyl derivative, and the silane compound subjected to said reaction can be purified using a conventional purification process, preferably column chromatography.

The mixing step 2) is performed by suitably mixing the organic-inorganic hybrid glass with the purified silane compound, the acid catalyst, the transition metal catalyst and the organic solvent. In this case, the acid used may be at least one selected from the group consisting of Bronsted acids, such as HCl, HBr and HI, and the transition metal catalyst used may be rhodium or iridium. As the organic solvent, toluene, benzene, methylene chloride, chloroform, THF and dimethylacetamide may be used alone or in a mixture of two or more thereof.

Meanwhile, although this mixing in the step 2) can also be performed together with a separate heating or reflux reaction, the mixing is preferably conducted at 10-30° without needing to carry out the heating or reflux reaction.

The surface modification method according to the fourth aspect of the present invention may further comprise, after the step 2), a step of stirring the mixture for a time period ranging from 5 minutes to 24 hours depending on the kind of silane compound and the kind of organic group introduced, to thereby facilitate the reaction.

Furthermore, the inventive method may preferably further comprise, before the step 1) or after the step 2), a step of introducing an organic group into the radical $R_5$ of Formula 1. The organic group may preferably be at least one selected from the group consisting of amino acids, proteins, chiral compounds and natural compounds.

MODE FOR INVENTION

Hereinafter, the present invention will be described in detail with reference to examples. It is to be understood, however, that these examples are for illustrative purposes and are not to be construed to limit the scope of the present invention.

Example 1~6

[Reaction Scheme 1]

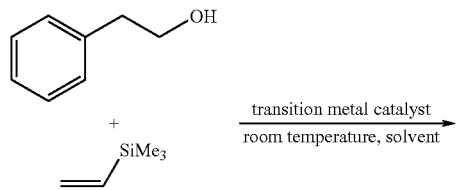

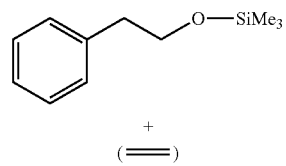

As shown in Table 1, transition metal catalyst in 100 mg of chloroform was added to the mixture of phenethyl alcohol (61.2 mg, 0.5 mmol) and trimethylvinylsilane (1.5 mmol), and if necessary, 4.0 M HCl in 1,4-dioxane was also added. The reaction mixture was stirred, and the progress of the reaction was determined by gas chromatography, and the results were shown in Table 1 below.

Among various catalysts, the reaction with a catalyst system of 1 mol % of chlorobis(cyclooctene)rhodium(I) dimer and HCl was completed after 2 hours (Example 1). The reaction was also completed with chlorobis(ethylene)rhodium(I) dimer and HCl. When the same reaction was carried out in the presence of chlorobis(cyclooctene)iridium(I) dimer and HCl, a 83% yield of product, phenethyl silyl ether, was determined by GC. The reaction also proceeded in the presence of rhodium halide (Cl, Br) hydrate to give 90% and 80% yields of product, respectively. The reason must be that rhodium(III) is reduced to rhodium(I) with generation of HCl or HBr by alcohol and vinylsilane, in which rhodium (I) and HCl (or HBr) act as catalysts to allow the reaction to proceed efficiently at room temperature. With exclusive chlorobis(cyclooctene)rhodium dimer, the reaction proceeded at 70° C. in a 100% conversion (Example 6). However, with other transition metal complexes having similar forms, the reactions did not take place. (Comparative Example 2~4).

TABLE 1

O-silylation of phenethyl alcohol with trimethylvinylsilane under various catalysts

| | Transition Metal Catalyst | Solvent | Reaction Condition | Yield (%, GC) |
|---|---|---|---|---|
| Example 1 | [(C$_8$H$_{14}$)$_2$RhCl]$_2$/HCl | chloroform | room temperature, 1 mol % of catalyst, 2 hours | 100 |
| Example 2 | [(C$_2$H$_4$)$_2$RhCl]$_2$/HCl | chloroform | room temperature, 1 mol % of catalyst, 2 hours | 100 |
| Example 3 | [(C$_8$H$_{14}$)$_2$IrCl]$_2$/HCl | chloroform | room temperature, 3 mol % of catalyst, 2 hours | 83 |
| Example 4 | RhX$_6$•xH$_2$O | chloroform | room temperature, 5 mol % of catalyst | X = Cl: 90% (6 hours) |
| Example 5 | RhX$_6$•xH$_2$O | chloroform | room temperature, 5 mol % of catalyst | X = Br: 80% (18 hours) |
| Example 6 | [(C$_8$H$_{14}$)$_2$RhCl]$_2$ | toluene | 70° C., 3 mol % of catalyst, 3 hours | 100 |
| Comparative Example 1 | [(C$_8$H$_{14}$)$_2$RhCl]$_2$ | chloroform | room temperature, 3 mol % of catalyst, 2 hours | 0 |
| Comparative Example 2 | [(p-cymene)$_2$Ru(m-Cl)]$_2$Cl$_2$/HCl | chloroform | room temperature, 1 mol % of catalyst, 2 hours | 0 |
| Comparative Example 3 | [($\eta^3$-C$_3$H$_5$)$_2$PdCl]$_2$/HCl | chloroform | room temperature, 1 mol % of catalyst, 2 hours | 0 |
| Comparative Example 4 | [(C$_2$H$_4$)$_2$PtCl]$_2$(m-Cl)$_2$/HCl | chloroform | room temperature, 1 mol % catalyst, 2 hours | 0 |

The special feature of this invention from the results in Table 1 is that O-silylation of alcohol with vinylsilane can be achieved at room temperature using rhodium(I) or iridium catalyst with acid catalyst. This reaction was found to be also achieved using Rh(III) catalyst, probably due to in-situ generation of acid catalyst and rhodium(I) by the reduction of rhodium(III) catalyst with alcohol and vinylsilane. With exclusive use of chlorobis(cyclooctene)rhodium dimer, the reaction proceeded above 70° C. However, with other transition metal species having similar forms, the reactions did not take place.

Example 7~8

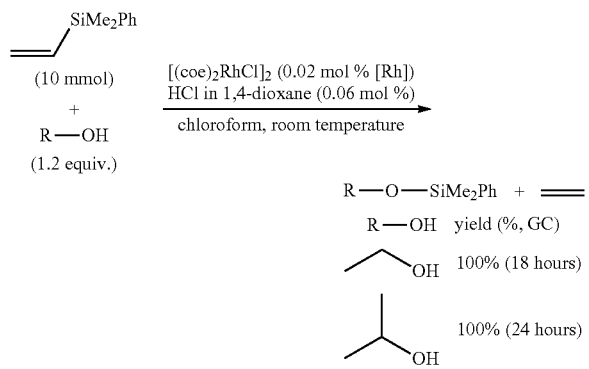

[Reaction Scheme 2]

As shown in Reaction Scheme 2, 0.7 mg of chlorobis (cyclooctene)rhodium dimer dissolved in 100 mg of chloroform was added to dimethylphenylvinylsilane (10 mmol), and then 12 mmol of ethanol (552 mg, Example 7) or 2-propanol (720 mg, Example 8) with 2 mg of 4.0 M HCl in 1,4-dioxane was added. The reaction mixture was stirred at room temperature, and the progress of the reaction was monitored by gas chromatography.

Figure 2:
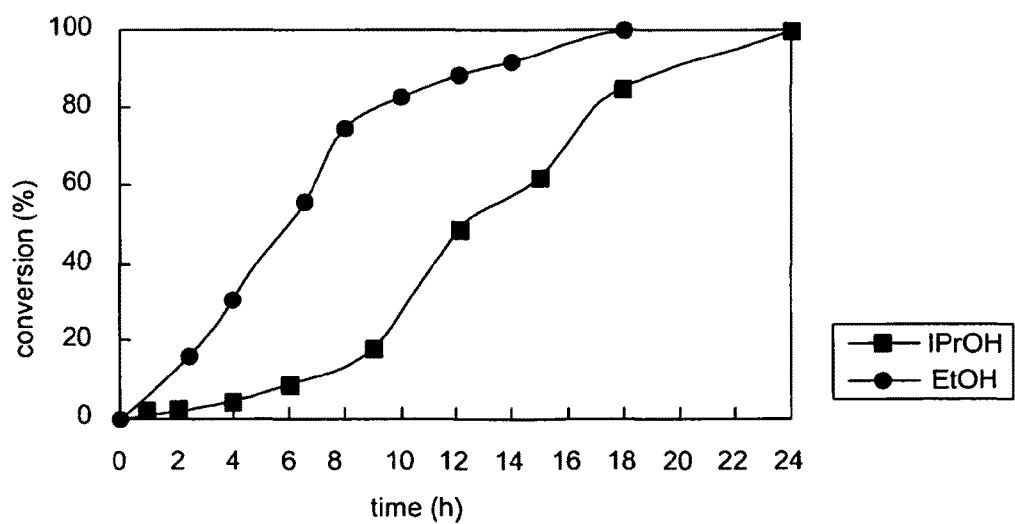
FIG. 2 is a graphic diagram showing the degree of the O-silylation of ethanol and 2-propanol with dimethylphenylsilane in the presence of 0.02 mol % of a chlorobis(cyclooctene)rhodium dimmer and 0.06 mol % of a HCl catalyst as a function of reaction time.

The above reaction was conducted in the presence of 0.02 mol % of metal catalyst and 0.06 mol % of acid catalyst to identify the efficiency of O-silylation. The reaction coordinate for describing the reaction progress is shown in FIG. 2.

O-silylation of ethanol or 2-propanol with dimethylphenylvinylsilane was completed in 18 hours or 24 hours, respectively. The above results show that the efficiency of introducing protecting group in alcohol or alcohol derivatives using this O-silylation method is very high.

Example 9~17

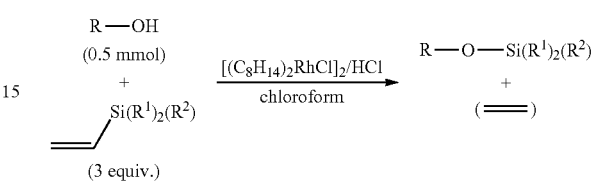

[Reaction Scheme 3]

As shown in Reaction Scheme 3 above, 0.7 mg of chlorobis (cyclooctene)rhodium dimer (1.8 mg, 0.0025 mmol) was fed into 1 ml V-vial, and 100 mg of chloroform was added. Then, 4 mg of 4.0 M HCl in 1,4-dioxane, alcohol (0.5 mmol) and vinylsilane (10 mmol) were added into the reactor, and the reaction mixture was stirred. The progress of the reaction was monitored by gas chromatography. The pure silylated product was isolated by column chromatography.

O-Silylation of various alcohols were carried out under reaction condition of Example 1 above in the presence of different amount of rhodium(I) catalyst and acid catalyst, the results are shown in Table 2, and isolated yield was a little bit lower than GC yield. With trimethylvinylsilane, the reaction of 1° alcohol was completed in the presence of 1 mol % of rhodium catalyst (Example 9-12), and the reaction of 2° alcohol was completed in the presence of 3 mol % of rhodium catalyst, determined by GC (Example 13-15). However, the reaction of 3° alcohol with dimethylphenethylvinylsilane could be completed using N,N'-dimethylacetamide (DMA) as a solvent in the presence of 5 mol % of rhodium catalyst (Example 16, 17). Also, O-silylation using other vinylsilanes such as dimethylphenylsilane and triethylvinylsilane was successfully achieved. (Example 10, 11)

TABLE 2

O-silylation of various alcohols with vinylsilane

| | alcohol | vinylsilane | amount of catalyst/ reaction time | yield (%) |
|---|---|---|---|---|
| Example 9 | PhCH₂CH₂OH | SiMe₃ | 1 mol %/2 hours | 96 (100) |
| Example 10 | PhCH₂CH₂OH | SiMe₂Ph | 1 mol %/2 hours | 84 (100) |
| Example 11 | PhCH₂CH₂OH | SiEt₃ | 3 mol %/2 hours | 75 (100) |

TABLE 2-continued

O-silylation of various alcohols with vinylsilane

| | alcohol | vinylsilane | amount of catalyst/ reaction time | yield (%) |
|---|---|---|---|---|
| Example 12 | cyclohexylpropanol (CyCH2CH2CH2OH) | SiMe3 | 1 mol %/4 hours | 96 (100) |
| Example 13 | 1-phenyl-2-propanol | SiMe3 | 3 mol %/4 hours | 97 (100) |
| Example 14 | cyclooctanol | SiMe3 | 3 mol %/4 hours | 98 (100) |
| Example 15 | menthol | SiMe3 | 3 mol %/4 hours | 88 (100) |
| Example 16 | 1-adamantanol | SiMe2Ph | 5 mol %/4 hours | 90 (100) |
| Example 17 | 2-methyl-1-phenyl-2-propanol | SiMe2Ph | 5 mol %/4 hours | 88 (100) |

All yields in Table 2 signify isolated yields (%) after column chromatography, and GC yields are given in parentheses.

As shown in Table 2, O-silylation could be achieved using various alcohols and vinylsilanes in high yields.

Example 18

Synthesis of 3-chloropropyldimethylvinylsilane

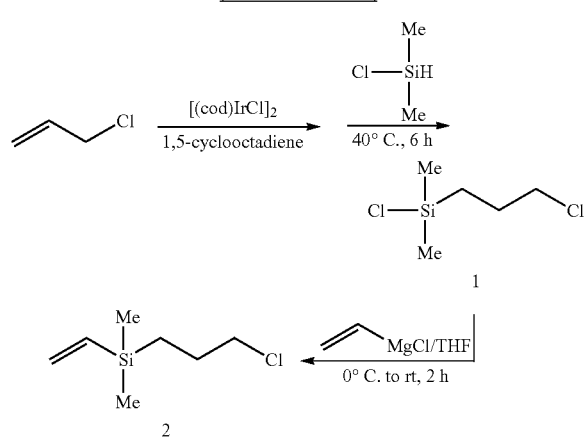

[Reaction Scheme 4]

(1) Synthesis of 1 in Reaction Scheme 4

The iridium catalyst (30 mg, chloro-1,5-cyclooctadiene iridium (I) dimer) was placed in a reactor which was charged with nitrogen. To this, 9.2 g (120 mmol) of allyl chloride, 30° of 1,5-cyclooctadiene, and 11 g (120 mmol) of chlorodimethylsilane were sequentially added. Then, the mixture was stirred at 40° for 6 hours. After completion of the reaction, the reaction product was subjected to fractional distillation to obtain 15 g (72% yield) of pure 3-chloropropylchloro dimethylsilane (1).

(2) Synthesis of 2 in Reaction Scheme 4

The above-synthesized 3-chloropropylchlorodimethylsilane (1) (15.6 g, 91.2 mmol) was dissolved in 50 mL of THF, to which 1.6 M vinylmagnesium chloride (85.6 mL, 137 mmol) was slowly added at 0°, and the mixture was stirred for 2 hours. After the reaction, the organic layer was extracted with aqueous NH$_4$Cl solution and ether, and the organic layer was washed with aqueous saturated NaCl solution. The washed organic solution was dried with anhydrous MgSO$_4$, and then filtered through celite to remove MgSO$_4$. After evaporating the solvent, the resulting residue was purified by column chromatography (n-Hex:EA=10:1, Rf=0.78) to give 14.2 g (96% yield) of pure 3-chloropropyldimethylvinylsilane (2).

2: $^1$H NMR (250 MHz, CDCl$_3$) (ppm) 6.20-5.64 (m, 3H), 3.53-3.47 (t, J=7.0 Hz, 2H), 1.83-1.71 (m, 2H), 0.70-0.63 (m, 2H), 0.08 (s, 6H); $^{13}$C NMR (62.9 MHz, CDCl$_3$) (ppm) 138.4, 132.2, 48.0, 27.7, 13.2, −3.5.

Example 19

Synthesis of 3-chloropropylmethyldivinylsilane

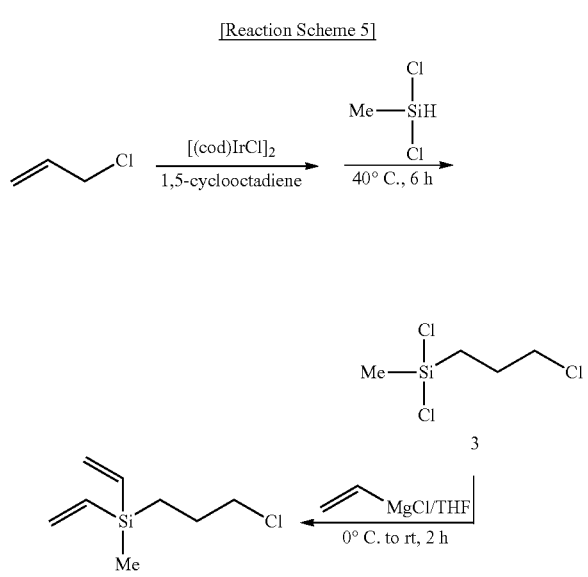

<Synthesis of 3 in Reaction Scheme 5>

As shown in Reaction Scheme 5 above, 30 mg of an iridium catalyst (chloro-1,5-cyclooctadiene iridium (I) dimer) was placed in a reactor which was charged with nitrogen. To this, 9.2 g (120 mmol) of allyl chloride and about 30□ of 1,5-cyclooctadiene were added, and then 14 g (120 mmol) of dichloromethylsilane was slowly added. The mixture was stirred at 40° for 6 hours. After the reaction, the reaction product was subjected to fractional distillation to give 17 g (68% yield) of pure 3-chloropropyl dichloromethylsilane (3).

<Synthesis of 4 in Reaction Scheme 5>

The above-synthesized 3-chloropropyldichloromethylsilane (3) (9 g, 52.2 mmol) was dissolved in 50 mL of THF, to which 1.6 M vinylmagnesium chloride (98 mL, 157 mmol) was then slowly added at 0°, and the mixture was stirred for 2 hours. After the reaction, the organic layer was extracted with NH$_4$Cl aqueous solution and ether, and washed with saturated NaCl. The washed organic layer was dried with anhydrous MgSO$_4$ and then filtered through celite to remove MgSO$_4$. After evaporating the solvent, and the resulting residue was purified by column chromatography (n-Hexane, Rf=0.36) to give 8.3 g (91% yield) of pure 3-chloropropylmethyldivinylsilane (4).

4: $^1$H NMR (250 MHz, CDCl$_3$) (ppm) 6.04-5.46 (m, 6H), 3.37-3.31 (t, J=6.9 Hz, 2H), 1.68-1.56 (m, 2H), 0.63-0.56 (m, 2H), 0.0 (s, 3H); $^{13}$C NMR (62.9 MHz, CDCl$_3$) (ppm) 136.4, 133.6, 48.0, 27.6, 11.9, −5.2.

Example 20

Synthesis of 3-chloropropyltrivinylsilane

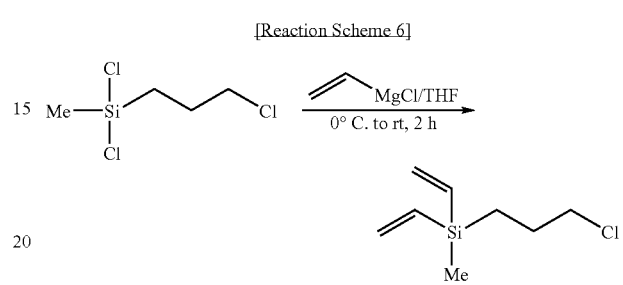

As shown in Reaction Scheme 6, a reactor was charged with nitrogen, into which (27.6 g, 130 mmol) 3-chloropropyltrichlorosilane and 20 mL of THF were added. Then, 1.6 M vinylmagnesium chloride (270 mL, 429 mmol) was added dropwise over 3 hours. After the reaction, the organic layer was extracted with aqueous NH$_4$Cl solution and ether, and it was washed with saturated NaCl aqueous solution. The washed organic layer was dried with anhydrous MgSO$_4$ and then filtered through celite to remove MgSO$_4$. After evaporating the solvent, and the resulting residue was subjected to fractional distillation to give 22.4 g (92% yield) of pure 3-chloropropyltrivinylsilane.

$^1$H NMR (250 MHz, CDCl$_3$) (ppm) 6.22-5.72 (m, 9H), 3.54-3.49 (t, J=6.9 Hz, 2H), 1.88-1.76 (m, 2H), 0.89-0.82 (m, 2H), $^{13}$C NMR (62.9 MHz, CDCl$_3$) (ppm) 135.194, 134.187, 48.015, 27.522, 10.565.

Example 21

Synthesis of dodecyldimethylvinylsilane

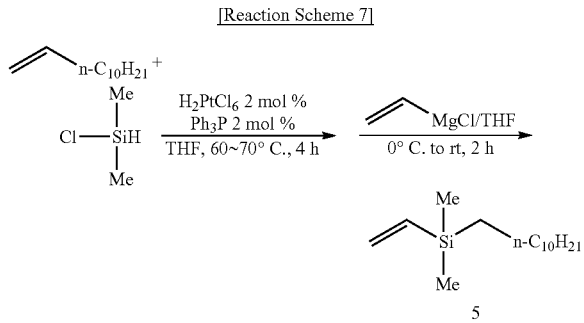

As shown in Reaction Scheme 7, to a reactor charged with nitrogen was added H$_2$PtCl$_6$ (189 mg, 0.36 mmol) and triphenylphosphine (PPh$_3$, 93.5 mg, 0.36 mmol), and 60 ml of THF was added. To this solution, 1-dodecene (3.0 g, 17.82 mmol) and chlorodimethylsilane (2.2 g, 23.17 mmol) was added, and then the mixture was heated up from room temperature to 70°. It was stirred at this temperature for 4 hours.

After the reaction, 17 ml of 1.6 M vinylmagnesium chloride was added, and the mixture was stirred for 2 hours. After the reaction, the organic layer was extracted with NH₄Cl aqueous solution and ether, and washed with saturated NaCl aqueous solution. The washed organic layer was dried with anhydrous MgSO₄, and then filtered through celite to remove MgSO₄. After evaporating the solvent, fractional distillation was conducted to remove unreacted 1-dodecene. The residue was purified by column chromatography (n-Hex:EA=10:1, Rf=0.84) to give 2.9 g (65% yield) of pure dodecyldimethyl vinylsilane (5).

5: $^1$H NMR (250 MHz, CDCl$_3$) (ppm) 6.22-5.61 (m, 3H), 1.26 (s, 20H), 0.91-0.86 (t, J=6.5 Hz, 3H), 0.58-0.52 (t, J=7.4 Hz, 2H), 0.48 (s, 1H); $^{13}$C NMR (62.9 MHz, CDCl$_3$) (ppm) 139.6, 131.4, 33.7, 32.1, 29.8, 29.7, 29.5, 23.9, 22.8, 15.5, 14.2, −3.31. IR spectrum (neat) 3043, 2958, 2917, 2851, 1895, 1593, 1466, 1250, 1376, 837 cm$^{-1}$. Anal. Calcd for C$_{16}$H$_{34}$Si: C, 75.50; H, 13.46; found: C, 74.3; H, 13.3 HR-MS: m/z calcd for C$_{16}$H$_{34}$Si [M−H]$^+$=253.2349 found: 253.2352.

Example 22

Synthesis of 3-acetoxypropyldimethylvinylsilane

[Reaction Scheme 8]

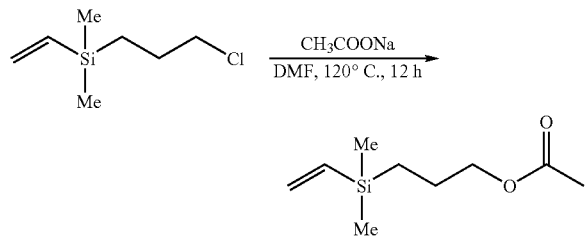

As shown in the Reaction Scheme 8, a mixture of 3-chloropropyldimethylvinylsilane (1.0 g, 6.15 mmol) and sodium acetate (1.01 g, 12.3 mmol) was dissolved in 17 mL of N,N'-dimethylformamide (DMF), and the resulting solution was heated at 120° C. for 12 hours. After the reaction, the organic layer was extracted with distilled water and ether. After evaporating the solvent, the resulting residue was purified by column chromatography (n-Hex:EA=10:1, Rf=0.36) to give 859 mg (75% yield) of pure 3-acetoxypropyldimethylvinylsilane.

$^1$H NMR (250 MHz, CDCl$_3$) (ppm) 6.19-5.62 (m, 3H), 4.03-3.97 (t, J=7.0 Hz, 2H), 2.03 (s, 3H), 1.67-1.55 (m, 2H), 0.59-0.54 (m, 2H), 0.03 (s, 6H); $^{13}$C NMR (62.9 MHz, CDCl$_3$) (ppm) 171.3, 138.6, 132.0, 67.1, 23.2, 21.1, 11.3, −3.5. IR spectrum (neat) 2949, 1740, 1593, 1237, 1045, 837 cm$^{-1}$ Example 23

Synthesis of 4-phenyl-1-(3-trivinylsilanyl)propyl-1-hydro-[1,2,3]triazole

[Reaction Scheme 9]

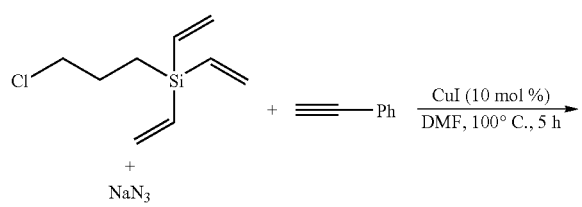

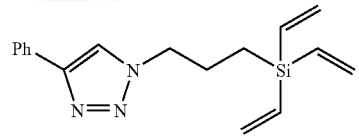

As shown in Reaction Scheme 9, a mixture of 3-chloropyltrivinylsilane (3.0 g, 16.06 mmol), phenylacetylene (180 mg, 17.61 mmol), and sodium azide (209 mg, 32.12 mmol) was dissolved in 6 ml of N,N'-dimethylforamide (DMF). To the resulting solution, copper iodide (306 mg, 1.6 mmol) was added. The reaction mixture was stirred at 100° C. for 5 hours. After the reaction, the organic layer was extracted by addition of methylene chloride and saturated NaCl aqueous solution. The organic layer was dried with anhydrous MgSO$_4$ and filtered through celite to remove MgSO$_4$. After evaporating the solvent, the residue was purified by column chromatography (n-Hexane:EA=2:1, Rf=0.5) to give 3.84 g (81% yield) of pure 4-phenyl-1-(3-trivinylsilanyl)propyl-1-hydro-[1,2,3] triazole.

$^1$H NMR (250 MHz, CDCl$_3$) (δ) 7.85-7.33 (m, 6H) 6.15-5.30 (m, 9H) 4.39 (t, J=7.2 Hz, 2H), 2.06-1.94 (m, 2H), 0.8-0.73 (m, 2H); $^{13}$C NMR (62.9 MHz, CDCl$_3$)(δ) 147.7, 135.4, 133.7, 130.8, 128.9, 128.2, 125.7, 119.6, 53.2, 25.1, 9.9. IR spectrum (neat) 3130, 3048, 2946, 1589, 1401, 1009, 735.1 cm$^{-1}$; Anal. Calcd for C$_{17}$H$_{21}$N$_3$Si: C, 69.11; H, 7.16; N, 14.22 found: C, 69.24H, 7.04; N, 14.1.

Example 24~29

The Reaction of Various Vinylsilanes and Ethanol

[Reaction Scheme 10]

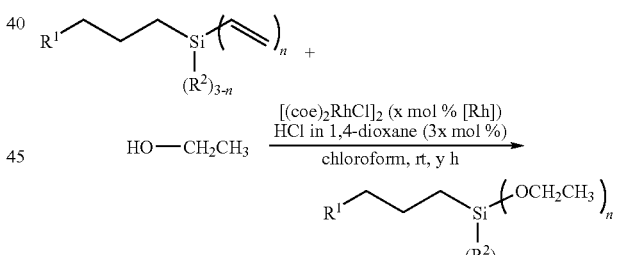

As shown in Reaction Scheme 10, different amounts (1~20 mol %) of chlorobis(cyclooctene)rhodium dimer in 100 mg of chloroform were fed into 1 ml V-vial. After addition of vinylsilane (0.2 mmol) and ethanol (1.2 equivalent per vinyl group) to this solution, 4 mg of 4.0 M HCl in 1,4-dioxane was added, and the resulting mixture was stirred. Each product was determined by gas chromatography, GCD analyzer, and $^1$H NMR. The results are shown in Table 3.

The reaction of 3-chloropropyldimethylvinylsilane with ethanol was carried out and completed in the presence of 2 mol % of rhodium(I) catalyst and 6 mol % of acid catalyst in 2 hours (Example 24), and the reaction of 3-chloropropylmethyldivinylsilane with ethanol was also carried out and completed in the presence of 3 mol % of rhodium(I) catalyst and 9 mol % of acid catalyst in 2 hours (Example 25). The reaction of 3-chloropropyltrivinylsilane with ethanol was carried out and completed in the presence of 5 mol % of rhodium(I) catalyst and 15 mol % of acid catalyst in 2 hours (Example 26). Dodecyldimethylvinylsilane also reacted with ethanol in the presence of 2 mol % of rhodium(I) catalyst and 6 mol % acid catalyst at room temperature for 2 hours to give a 100% yield of dodecyldimethylethoxysilane (Example 27). 3-Acetoxypropyldimethyl-vinylsilane reacted with ethanol under the identical reaction conditions with same catalyst to give corresponding ethoxysilane derivative in 70% yield (Example 28). It was found that the reaction of 4-phenyl-1-(3-trivinylsilanylpropyl)-1H-[1,2,3]triazole with ethanol was completed in the presence of 20 mol % of rhodium(I) catalyst and 60 mol % of acid catalyst after 6 hours (Example 29).

TABLE 3

The reaction of ethanol with various vinylsilane

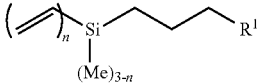

| | | x mol %/y hour(s) | conversion yield (%, GC) |
|---|---|---|---|
| Example 24 | 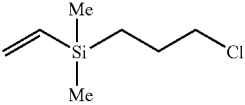 | 2 mol %/2 hours | 100 |
| Example 25 | 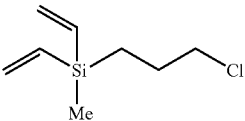 | 3 mol %/2 hours | 100 |
| Example 26 | 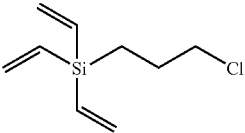 | 5 mol %/2 hours | 100 |
| Example 27 | 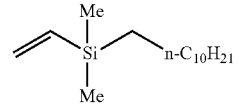 | 2 mol %/2 hours | 100 |
| Example 28 | 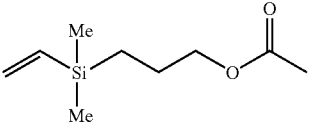 | 2 mol %/2 hours | 70 |
| Example 29 | 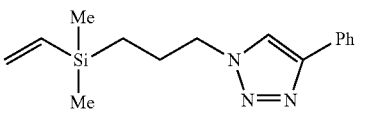 | 20 mol %/6 hours | 100 |

As shown in Table 3, all reactions of 3-chloropropylvinyl-silanes having 1 to 3 vinyl groups with ethanol took place efficiently. Likewise, vinylsilanes having alkyl (dodecyl), acetoxy, and phenyltriazolyl group showed good reactivities for O-silylation of ethanol.

Example 30~31

Determination of Intermediate for O-Silylation of Alcohol

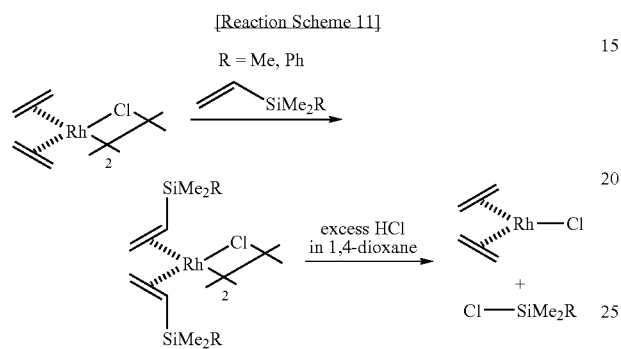

[Reaction Scheme 11]

R = Me, Ph

As shown in Reaction Scheme 11, chlorobis(cyclooctene) rhodium dimer was added to excess amount of trimethylvi-nylsilane (R=Me, Example 30) or dimethylphenylvinylsilane (R=Ph, Example 31). The reaction mixture was stirred for 2 hours, and then unreacted vinylsilanes were removed in vacuo. The resulting intermediate complex, chlorobis(trim-ethylvinylsilane) rhodium(I) or chlorobis(dimethylphenylvi-nylsilane)rhodium(I) complex was dissolved in $CDCl_3$, and each complex was characterized by $^1H$ NMR. To this solution, excess amount of 4.0 M HCl in 1,4-dioxane was added, and the resulting reaction mixture was taken by $^1H$ NMR.

Figure 3:
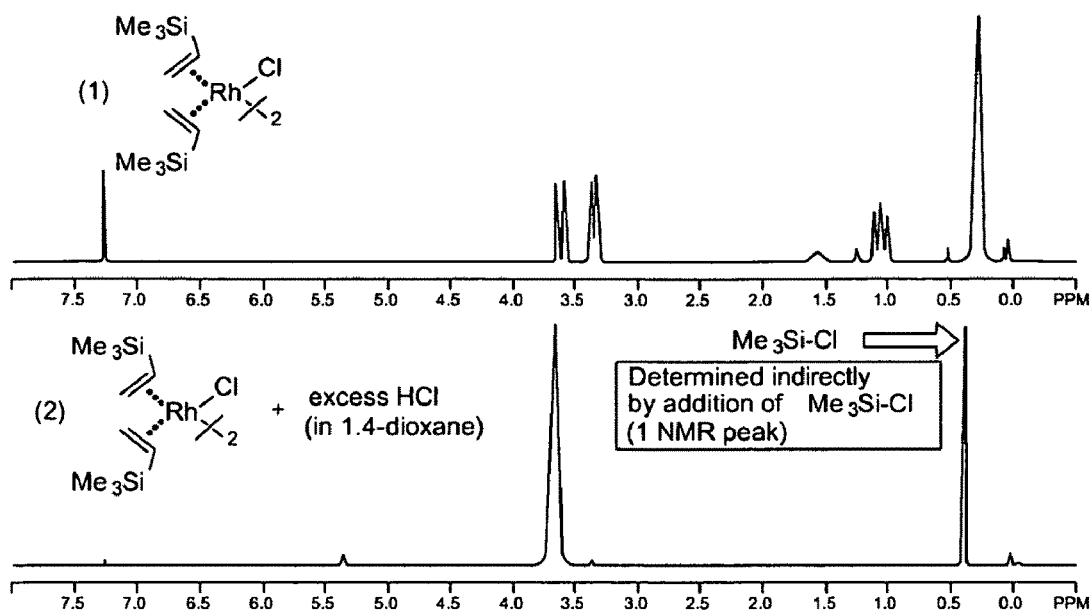
FIG. 3 shows $^1$H NMR spectra obtained by measuring the reaction between bis(trimethylsilane)rhodium and an acid in order to identify an intermediate of the O-silylation of alcohol with vinylsilane in the presence of a transition metal catalyst and an acid catalyst.

The $^1H$ NMR spectra of the intermediate from the reaction of trimethylvinylsilane and rhodium(I) catalyst is shown in FIG. 3. FIG. 3-(1) is a spectrum of $[h^2-(CH_2=CH-SiMe_3)_2 RhCl]_2$. The vinyl peak in $[h^2-(CH_2=CH-SiMe_3)_2RhCl]_2$ is shifted to the upfield (3.3~3.6 ppm and 1.0~1.2 ppm), compared with free trimethylvinylsilane (multiplet of 5.7~6.3 ppm). Referring to FIG. 3-(2), after addition of excess amount of HCl in 1,4-dioxane, a peak of singlet at 0.1 ppm is shifted to 0.37 ppm due to a change of coordinated trimethylvinylsilane to chlorotrimethylsilane, which can be identified by comparison with $^1H$ NMR spectra of the authentic chlorotrimethylsilane.

Figure 4:
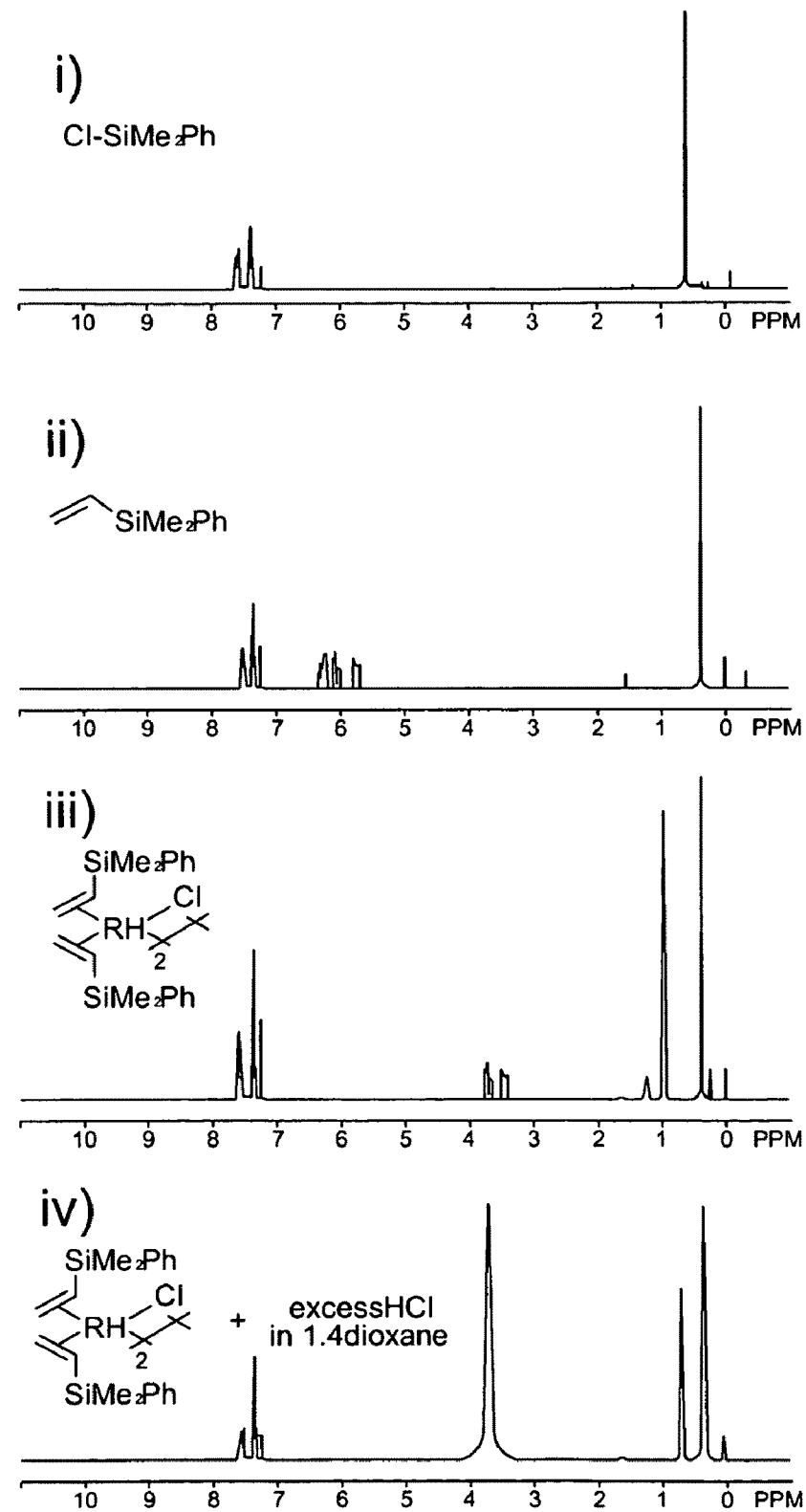
FIG. 4 shows $^1$H NMR spectra obtained by measuring the reaction between bis(dimethylphenylsilane)rhodium and an acid in order to identify an intermediate of the O-silylation of alcohol with vinylsilane in the presence of a transition metal catalyst and an acid catalyst.

The $^1H$ NMR spectra of the intermediate from the reaction of dimethylphenylvinylsilane and rhodium(I) catalyst is shown in FIG. 4. FIG. 4-(iii) is a spectrum of $[h^2-(CH_2=CH-SiMe_2Ph)_2RhCl]_2$. The vinyl peak in $[h^2-(CH_2=CH-SiMe_2Ph)_2RhCl]_2$ is shifted to the upfield (3.4~3.7 ppm and 1.1~1.3 ppm), compared with free dimethylphenylvinylsilane (multiplet of 5.7~6.3 ppm), and a new peak appears at 0.94 ppm. Referring to FIG. 4-(ii), by addition of excess amount of HCl in 1,4-dioxane, a peak at 0.9 ppm is shifted to 0.684 ppm due to a change of coordinated dimethylphenylvinylsilane to free chlorodimethylphenylsilane (FIG. 4-(iv)), which can be identified by comparison with $^1H$ NMR spectrum of authentic chlorodimethylphenylsilane (See FIG. 4-(i)).

The presumed mechanism based on the above results is shown in FIG. 1. Initially, olefin exchange reaction of cyclooctene in chlorobis(cyclooctene)rhodium(I) dimer with vinylsilane leads to the formation of chlorobis(trimethylvi-nylsilane)rhodium(I) dimer. The reaction of chlorobis(trim-ethylvinylsilane)rhodium(I) dimer with HCl might generate trimethylsilylethylrhodium(III) complex via rhodium-hy-dride complex, followed by b-silyl elimination in trimethyl-silylethylrhodium(III) complex to render the $Rh-SiMe_3$ complex with ethylene. Reductive elimination in the $Rh-SiMe_3$ complex affords rhodium-ethylene complex and chlorotrimethylsilane. Chlorotrimethylsilane reacts with alcohol to give silyl ether with regeneration of HCl, which reenter the catalytic cycle.

Based on the newly developed above O-silylation, the immobilization methods of the organic functional group or organic molecules on the solid support such as silica or ITO glass were devised and explained with the following examples.

Example 32~35

The Reaction of Amorphous Silica with 3-chloropropyldimethylvinylsilane

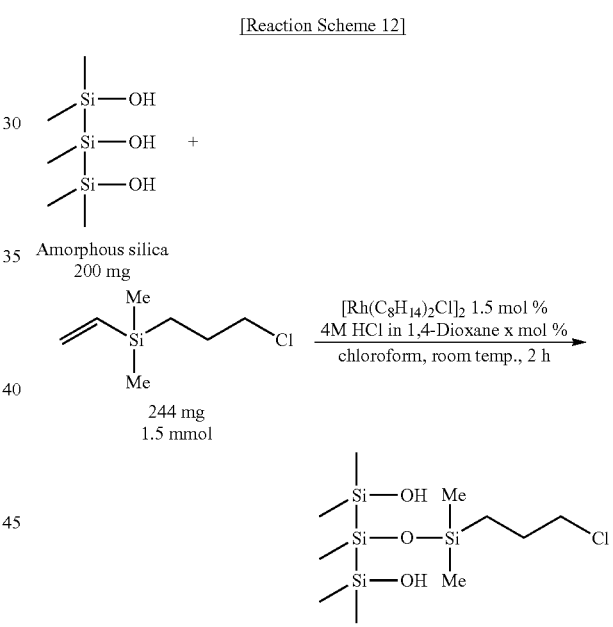

[Reaction Scheme 12]

As shown in Reaction Scheme 12 above, in a 1 mL V-vial, 244 mg (1.5 mmol) of 3-chloropropyldimethylvinylsilane, 200 mg of amorphous silica and 16.1 mg (1.5 mol %) of $[Rh(C_8H_{14})_2Cl]_2$ were dissolved in 400 mg of chloroform. And after addition of 11.7 mg (3 mol %) of 4 M HCl in 1,4-dioxane, the reaction mixture was stirred at room temperature for 2 hours. After the reaction, the silica solid was placed in a cellulose thimble, and subjected to solid-liquid extraction in an ethanol solvent using a Soxhlet extractor for 6 hours to remove unreacted material. The remaining solid was dried in a vacumm and analyzed for elemental composition (carbon, nitrogen and hydrogen). The loading rate from elemental analysis was found to be 0.914 mmol/g. (see Example 36, Table 5 below)

Said sample obtained by the above reaction was dried and subjected to elemental analysis, the analysis results showed that the weight percentage of carbon was 4.67 wt %, base on this results, the rate of organic substance loading onto the silica was calculated as follows. The carbon content of 0.0467 g was first divided by the molecular weight of carbon (12 g/mol), and then divided by 5, which is the number of carbons fixed to amorphous silica, and as a result, it can be seen that 0.78 mmol of the starting material per g of the solid silica was bonded to the solid silica surface in the reaction, so that the loading rate from elemental analysis was found to be 0.778 mmol/g. (see Example 32, Table 4 below)

The procedure of Example 32 above was repeated, except that the reaction according to Reaction Scheme 12 was conducted in the presence of 6 mol % of 4 M HCl in 1,4-dioxane, and the loading rate from the elemental analysis of the resulting product was found to be 0.848 mmol/g. (see Example 33, Table 4 below)

The procedure of Example 32 above was repeated, except that the reaction according to Reaction Scheme 12 was conducted in the presence of 9 mol % of 4 M HCl in 1,4-dioxane, and the loading rate from elemental analysis was found to be 0.956 mmol/g. (see Example 34, Table 4 below)

The procedure of Example 32 above was repeated, except that the reaction according to Reaction Scheme 12 was conducted in the presence of 12 mol % of 4 M HCl in 1,4-dioxane, and the loading rate from elemental analysis was found to be 0.899 mmol/g. (see Example 35, Table 4 below)

As shown in Table 4, use of 9 mol % of HCl showed the highest loading rate, and comparable reactivity was shown with 12 mol % of HCl.

Example 36~39

The Loading Rate (mmol/g) with Various Amount of Amorphous Silica

[Reaction Scheme 13]

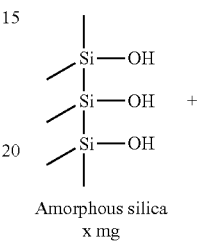

Amorphous silica
x mg

TABLE 4

The reaction of amorphous silica with 3-chloropropyldimethylvinylsilane under various amounts of HCl

| Example | product | reaction temperature (° C.) | reaction time (h) | amount of catalyst ([(C$_8$H$_{14}$)$_2$RhCl]$_2$/HCl) | amorphous silica | loading rate (mmol/g) |
|---|---|---|---|---|---|---|
| Example 32 | Si—OH Me<br>Si—O—Si—(CH$_2$)$_3$Cl<br>Si—OH Me | room temperature | 2 | 1.5 mol %/3 mol % | 200 mg | 0.778 |
| Example 33 | | | | 1.5 mol %/6 mol % | | 0.848 |
| Example 34 | | | | 1.5 mol %/9 mol % | | 0.956 |
| Example 35 | | | | 1.5 mol %/12 mol % | | 0.899 |

-continued

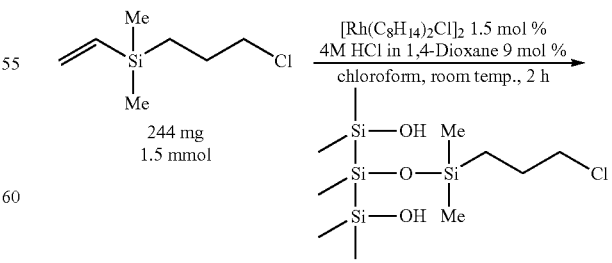

Reactions of example 36~39 were conducted in the same manner, except amount of amorphous silica. The results of elemental analysis for the reaction products are shown in Table 5. The reactions were carried out in the presence of 9 mol % of HCl, which resulted in the highest loading rate in Table 4.

As shown in Reaction Scheme 13 above, in a 1 mL V-vial, 244 mg (1.5 mmol) of 3-chloropropyldimethylvinylsilane, 100 mg of amorphous silica and 16.1 mg (1.5 mol %) of [Rh(C$_8$H$_{14}$)$_2$Cl]$_2$ were dissolved in 400 mg of chloroform. After addition of 4 M HCl in 1,4-dioxane to this solution, the reaction mixture was stirred at room temperature for 2 hours. After the reaction, the silica solid was placed in a cellulose thimble and subjected to solid-liquid extraction in an ethanol solvent using a Soxhlet extractor for 6 hours to remove unreacted material. The remaining solid was dried in a vacuum, followed by analysis for elemental composition (carbon, nitrogen and hydrogen). The loading rate from elemental analysis was found to be 0.914 mmol/g. (see Example 36, Table 5 below)

The procedure of Example 36 above was repeated, except that 400 mg of amorphous silica was used. The loading rate from elemental analysis was found to be 0.731 mmol/g. (see Example 37, Table 5 below)

The procedure of Example 36 above was repeated, except that 600 mg of amorphous silica was used. The loading rate from elemental analysis was found to be 0.604 mmol/g. (see Example 38, Table 5 below)

The procedure of Example 36 above was repeated, except that 800 mg of amorphous silica was used. The loading rate from elemental analysis was found to be 0.481 mmol/g. (see Example 39, Table 5 below)

TABLE 5

Loading rate from the reaction of amorphous silica with 1.5 mmol of 3-chloropropyldimethylvinylsilane

| Example | product | reaction temperature (° C.) | reaction time (h) | amount of catalyst ([(C$_8$H$_{14}$)$_2$RhCl]$_2$/HCl) | amorphous silica (mg) | loading rate (mmol/g) |
|---|---|---|---|---|---|---|
| Example 36 | 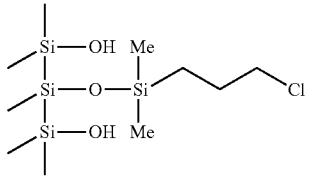 | room temperature | 2 | 1.5 mol %/9 mol % | 100 | 0.914 |
| Example 34 | | | | | 200 | 0.956 |
| Example 37 | | | | | 400 | 0.731 |
| Example 38 | | | | | 600 | 0.604 |
| Example 39 | | | | | 800 | 0.481 |

As shown in Table 5, the most proper amount of amorphous silica reacting with 1.5 mmol of 3-chloropropyldimethylvinylsilane was 200 mg, and the loading rate decreased by the increment of amorphous silica because of deficiency of 3-chloropropyldimethylvinylsilane.

Example 40

Characterization of 3-chloropropyldimethylsilyl Group-Impregnated Amorphous Silica by Solid-State $^{13}$C and $^{29}$Si CP-MAS NMR

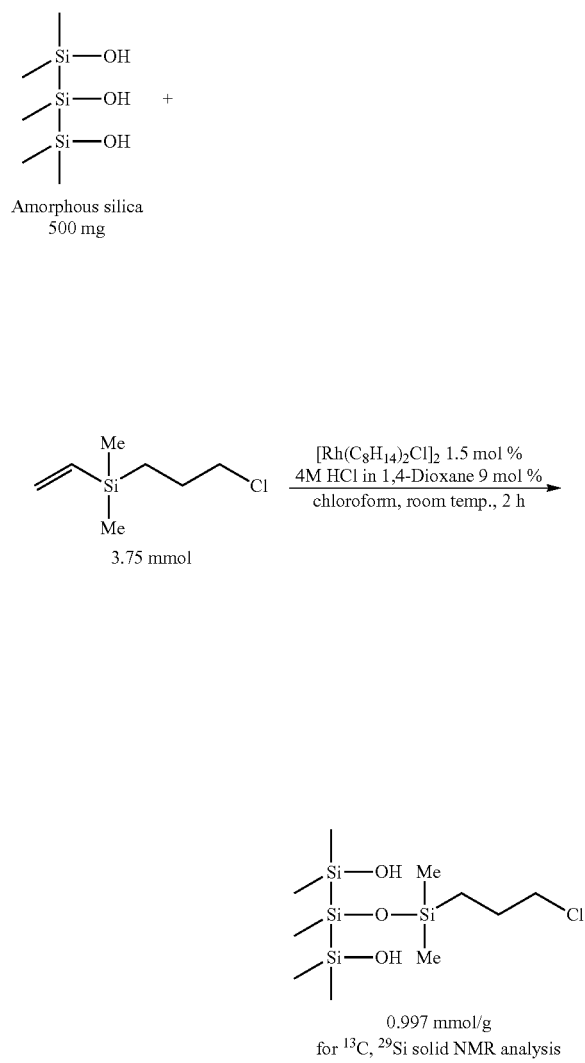

Figure 5:
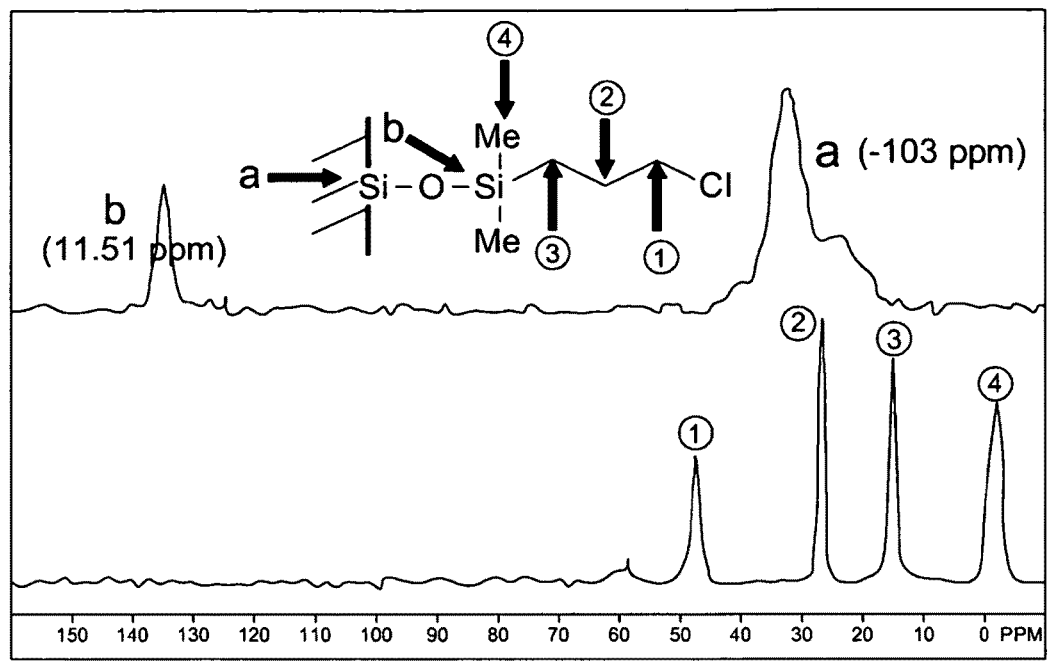
FIG. 5 is a photograph of solid $^{13}C^{29}Si$ CP-MAS NMR taken after allowing 3-chloropropyldimethylvinylsilane to react with amorphous silica at room temperature in a chloroform solvent, using $[Rh(C_8H_{14})_2Cl]_2$ and HCl as catalysts.

As shown in Reaction Scheme 14, the reaction of 3-chloropropyldimethylvinylsilane (3.75 mmol) with 500 mg of amorphous silica was carried out in the presence of 1.5 mol % [Rh(C$_8$H$_{14}$)$_2$Cl]$_2$ and 9 mol % of HCl at room temperature for 2 hours. The result could be found to be 0.997 mmol/g by elemental analysis. After the reaction, 3-chloropropyldimethylsilyl group-impregnated amorphous silica was characterized by solid state $^{13}$C and $^{29}$Si CP-MAS NMR. As shown in FIG. 5, 3-chloropropyldimethylsilyl group was covalently bonded to the amorphous silica.

Example 41~44

The Reaction of 3-chloropropylmethyldivinylsilane and Amorphous Silica

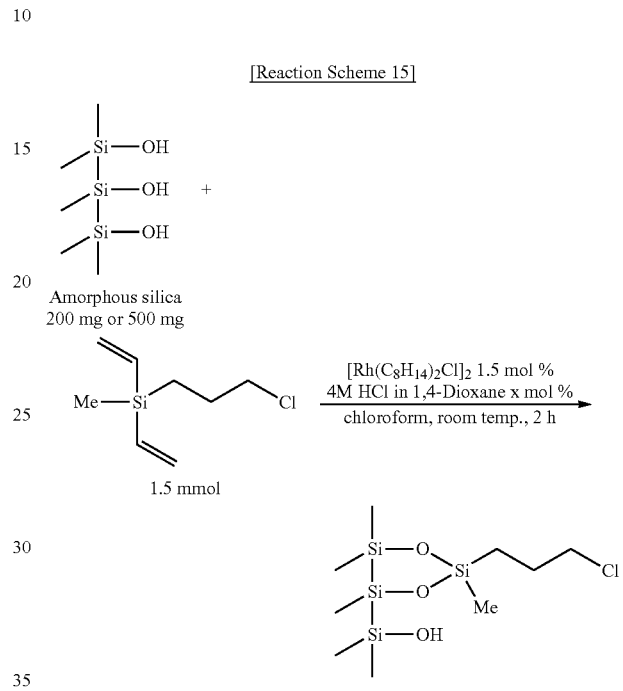

As shown in Reaction Scheme 15 above, in a 1 mL V-vial, 261 mg (1.5 mmol) of 3-chloropropylmethyldivinylsilane, 200 mg of amorphous silica and 16.1 mg (1.5 mol %) of [Rh(C$_8$H$_{14}$)$_2$Cl]$_2$ were dissolved in 400 mg of chloroform. After addition of 11.7 mg (3 mol %) of 4 M HCl in 1,4-dioxane to this solution, the reaction mixture was stirred at room temperature for 2 hours. After the reaction, the silica solid was placed in a cellulose thimble and subjected to solid-liquid extraction in an ethanol solvent using a Soxhlet extractor for 6 hours to remove unreacted material, and the remaining solid was dried in a vacuum, followed by analysis for elemental composition (carbon, nitrogen and hydrogen). The loading rate from elemental analysis could be calculated to be 0.926 mmol/g. (see Example 41, Table 6 below) The procedure of Example 41 (Reaction Scheme 15) above was repeated, except that 3.75 mmol of 3-chloropropylmethyldivinylsilane, 500 mg of amorphous silica, and 700 mg of chloroform were used. The loading rate from elemental analysis could be calculated to be 1.215 mmol/g. (see Example 42, Table 6 below)

The procedure of Example 41 (Reaction Scheme 15) above was repeated, except that 9 mol % of HCl was used. The loading rate from elemental analysis was found to be 1.462 mmol/g. (see Example 43, Table 6 below)

The procedure of Example 41 (Reaction Scheme 15) above was repeated, except that 9 mol % of HCl, 3.75 mmol of 3-chloropropylmethyldivinylsilane, 500 mg of amorphous silica, and 700 mg of chloroform were used. The loading rate from elemental analysis was found to be 1.528 mmol/g. (see Example 44, Table 6 below)

TABLE 6

The reaction of amorphous silica with 3-chloropropylmethyldivinylsilane under different amount of acid

| Example | product | reaction temperature (° C.) | reaction time (h) | amount of catalyst ([(C$_8$H$_{14}$)$_2$RhCl]$_2$/HCl) | amorphous silica (mg) | loading rate (mmol/g) |
|---|---|---|---|---|---|---|
| Example 41 | Si—O\Si—O/Si(Me)(CH$_2$CH$_2$CH$_2$Cl), Si—OH | room temperature | 2 | 1.5 mol %/3 mol % | 200 | 0.926 |
| Example 42 | | | | | 500 | 1.215 |
| Example 43 | | | | 1.5 mol %/9 mol % | 200 | 1.462 |
| Example 44 | | | | | 500 | 1.528 |

As shown in Table 6, in the reaction of 3-chloropropylmethyldivinylsilane with amorphous silica, it was found that the loading rate increased by the increment of amount of HCl. Besides, difference from the experiments in Table 5 (Example 34, 36-39) is overall increments of amounts of vinylsilane, catalysts and amorphous silica (scale up). Accordingly, loading rate increased by the increment of amount of amorphous silica (that is different result from the results of Table 5).

Example 45~48

The Reaction of 3-Chloropropyltrivinylsilane with Amorphous Silica

[Reaction Scheme 16]

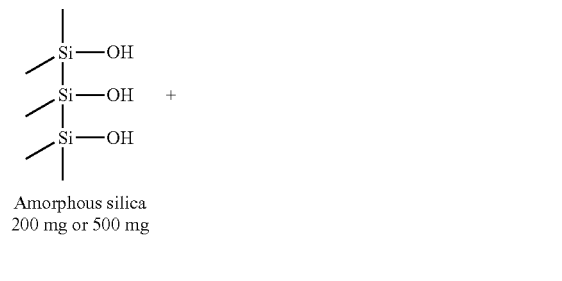

Amorphous silica
200 mg or 500 mg

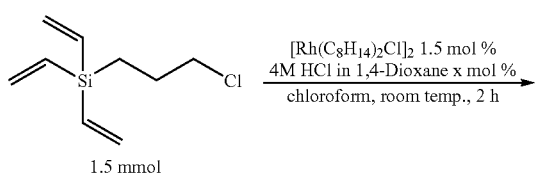

1.5 mmol

[Rh(C$_8$H$_{14}$)$_2$Cl]$_2$ 1.5 mol %
4M HCl in 1,4-Dioxane x mol %
chloroform, room temp., 2 h As shown in Reaction Scheme 16 above, in a 1 mL V-vial, 279 mg (1.5 mmol) of above-synthesized 3-chloropropyltrivinylsilane (Example 20, Reaction Scheme 6), 200 mg of amorphous silica and 16.1 mg (1.5 mol %) of [Rh(C$_8$H$_{14}$)$_2$Cl]$_2$ were dissolved in 400 mg of chloroform. After addition of 11.7 mg (3 mol %) of 4 M HCl in 1,4-dioxane to this solution, the reaction mixture was stirred at room temperature for 2 hours. After the reaction, the silica solid was placed in a cellulose thimble and subjected to solid-liquid extraction in an ethanol solvent using a Soxhlet extractor for 6 hours to remove unreacted material, and the remaining solid was dried in a vacuum, followed by analysis for elemental composition (carbon, nitrogen and hydrogen). The loading rate from elemental analysis was found to be 0.987 mmol/g. (see Example 45, Table 7 below)

The procedure of Example 45 (Reaction Scheme 16) was repeated, except that 3.75 mmol of 3-chloropropylmethyldivinylsilane, 500 mg of amorphous silica, and 700 mg of chloroform were used. The loading rate from elemental analysis was found to be 1.195 mmol/g. (see Example 46, Table 7 below)

The procedure of Example 45 (Reaction Scheme 16) was repeated, except that 9 mol % of HCl was used. The loading rate from elemental analysis was found to be 1.336 mmol/g. (see Example 47, Table 7 below)

The procedure of Example 45 (Reaction Scheme 16) was repeated, except that 9 mol % of HCl, 3.75 mmol of 3-chloropropylmethyldivinylsilane, 500 mg of amorphous silica, and 700 mg of chloroform were used. The loading rate from elemental analysis was found to be 1.535 mmol/g. (see Example 48, Table 7 below)

TABLE 7

The reaction of amorphous silica with 3-chloropropyltrivinylsilane under different amount of acid

| Example | product | reaction temperature (° C.) | reaction time (h) | amount of catalyst ([(C$_8$H$_{14}$)$_2$RhCl]$_2$/HCl) | amorphous silica (mg) | loading rate (mmol/g) |
|---|---|---|---|---|---|---|
| Example 45 | (structure shown) | room temperature | 2 | 1.5 mol %/3 mol % | 200 | 0.987 |
| Example 46 | | | | | 500 | 1.195 |
| Example 47 | | | | 1.5 mol %/9 mol % | 200 | 1.336 |
| Example 48 | | | | | 500 | 1.535 |

As shown in Table 7, in the reaction of 3-chloropropyltrivinylsilane with amorphous silica, the loading rate was also found to increase by the increment of HCl amount. Besides, difference from the experiments in Table 5 (Example 34, 36-39) is overall increments of amounts of vinylsilane, catalysts and amorphous silica (scale up). Accordingly, loading rate increased by the increment of amount of amorphous silica (that is different result from the results of Table 5).

Example 49~53

The Reaction of 3-Chloropropylvinylsilane Derivatives with Amorphous Silica at 40° C.

[Reaction Scheme 17]

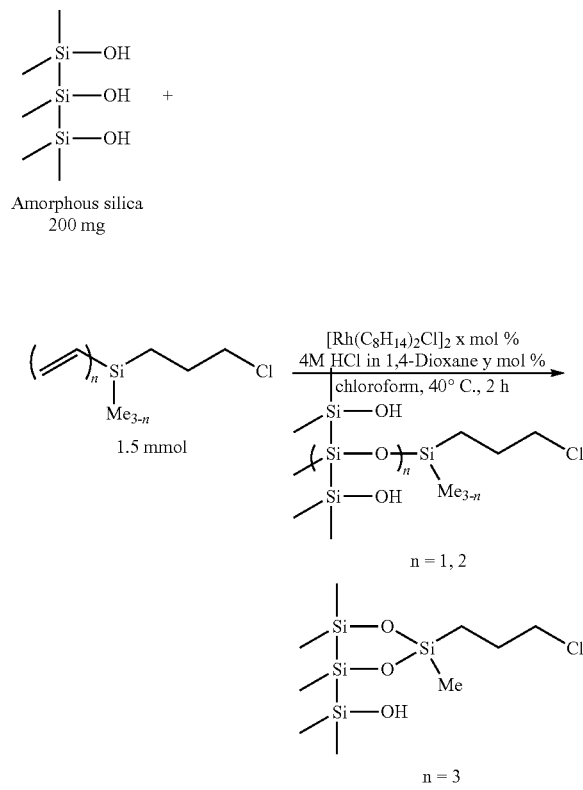

As shown in Reaction Scheme 17, in a 1 mL V-vial, 1.5 mmol of 3-chloropropylvinylsilane, 200 mg of amorphous silica and 0.5 mol % of [Rh(C$_8$H$_{14}$)$_2$Cl]$_2$ were dissolved in 400 mg of chloroform. After addition of 1 mol % of 4 M HCl in 1,4-dioxane to this solution, the reaction mixture was stirred at 40° C. for 2 hours.

After the reaction, the silica solid was placed in a cellulose thimble and subjected to solid-liquid extraction in an ethanol solvent using a Soxhlet extractor for 6 hours to remove unreacted material, and the remaining solid was dried in a vacuum, followed by analysis for elemental composition (carbon, nitrogen and hydrogen). The loading rate from elemental analysis was found to be 0.152 mmoug. (see Example 49, Table 8 below)

The procedure of Example 49 above was repeated, except that 1.5 mol % of [Rh(C$_8$H$_{14}$)$_2$Cl]$_2$ and 3 mol % of 4.0 M HCl in 1,4-dioxane were used. The loading rate from elemental analysis was found to be 0.795 mmol/g. (see Example 50, Table 8 below)

The procedure of Example 49 above was repeated, except that 2.5 mol % of [Rh(C$_8$H$_{14}$)$_2$Cl]$_2$ and 5 mol % of 4.0 M HCl in 1,4-dioxane were used. The loading rate from elemental analysis was found to be 0.807 mmol/g. (see Example 51, Table 8 below)

The procedure of Example 50 above was repeated, except that 3-chloropropylmethyldivinylsilane was used in place of 3-chloropropyldimethylvinylsilane. The loading rate from elemental analysis was found to be 1.231 mmol/g. (see Example 52, Table 8 below)

The procedure of Example 50 above was repeated, except that 3-chloropropyltrivinylsilane was used in place of 3-chloropropyldimethylvinylsilane. The loading rate from elemental analysis was found to be 1.271 mmol/g. (see Example 53, Table 8 below)

TABLE 8

The reaction of amorphous silica with 3-chloropropyltrivinylsilane under different amounts of catalysts at 40° C.

| Example | product | reaction temperature (° C.) | reaction time (h) | amount of catalyst ([(C$_8$H$_{14}$)$_2$RhCl]$_2$/HCl) | amount of amorphous silica | loading rate (mmol/g) |
|---|---|---|---|---|---|---|
| Example 49 | ≡Si—OH  Me<br>≡Si—O—Si—(CH$_2$)$_3$Cl<br>≡Si—OH  Me | 40 | 2 | 0.5 mol %/1 mol % | 200 | 0.152 |
| Example 50 | | | | 1.5 mol%/3 mol % | | 0.795 |
| Example 51 | | | | 2.5 mol %/5 mol % | | 0.807 |
| Example 52 | ≡Si—O<br>≡Si—O—Si—(CH$_2$)$_3$Cl<br>      Me<br>≡Si—OH | | | 1.5 mol %/3 mol % | | 1.231 |
| Example 53 | ≡Si—O<br>≡Si—O—Si—(CH$_2$)$_3$Cl<br>          \|\|<br>≡Si—OH | | | 1.5 mol %/3 mol % | | 1.271 |

Although the loading rate increased by the increment of amount of catalysts from the results of Example 49-53 in Table 8 above, this results suggested that proper amount of catalysts for this reaction could be found to be 1.5 mol % [Rh(C$_8$H$_{14}$)$_2$Cl]$_2$ and of 3 mol % of HCl in 1,4-dioxane, because any remarkable increment of loading rate was not observed with more than 1.5 mol % [Rh(C$_8$H$_{14}$)$_2$Cl]$_2$ and 3 mol % of HCl. From the results of Example 50, 52 and 53, it could be found that the loading rate increased along with the increment of number of vinyl groups.

Example 54~56

The reaction of Amorphous Silica with Vinylsilane Derivatives in the Presence of Ir Catalyst

Example 54

[Reaction Scheme 18]

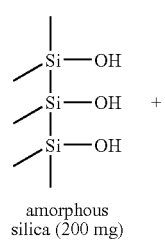

amorphous silica (200 mg)

+

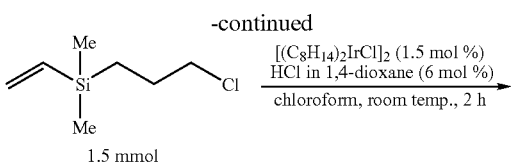

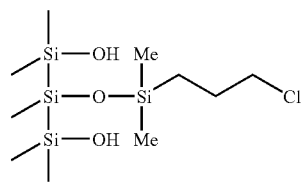

As shown in Reaction Scheme 18 above, in a 1 mL V-vial, 244 mg (1.5 mmol) of 3-chloropropyldimethylvinylsilane, 200 mg of amorphous silica and 1.5 mol % of [Ir(C$_8$H$_{14}$)$_2$Cl]$_2$ were dissolved in 400 mg of chloroform. After addition of 6 mol % of 4 M HCl in 1,4-dioxane to this solution, the reaction mixture was stirred at room temperature for 2 hours.

After the reaction, the silica solid was placed in a cellulose thimble and subjected to solid-liquid extraction in an ethanol solvent using a Soxhlet extractor for 6 hours to remove unreacted material, and the remaining solid was dried in a vacuum, followed by analysis for elemental composition (carbon, nitrogen and hydrogen). The loading rate from elemental analysis was found to be 0.95 mmol/g.

Example 55

[Reaction Scheme 19]

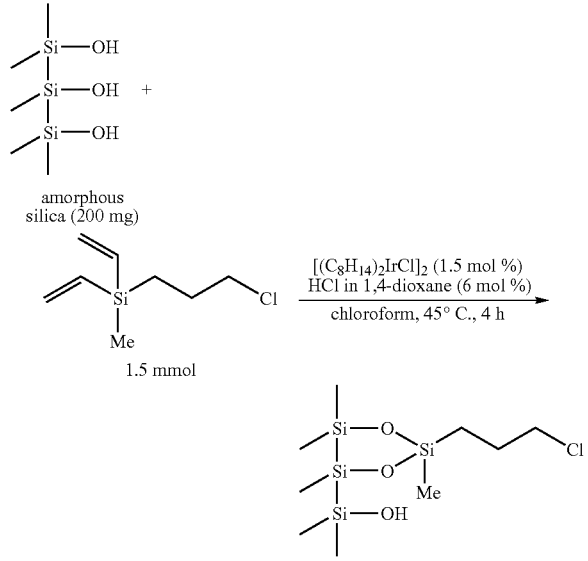

As shown in Reaction Scheme 19 above, in a 1 mL V-vial, 261 mg (1.5 mmol) of 3-chloropropylmethyldivinylsilane, 200 mg of amorphous silica and 1.5 mol % of [Ir(C$_8$H$_{14}$)$_2$Cl]$_2$ were dissolved in 400 mg of chloroform. After addition of 6 mol % of 4 M HCl in 1,4-dioxane to this solution, the reaction mixture was stirred at 45° C. for 4 hours.

After the reaction, the silica solid was placed in a cellulose thimble and subjected to solid-liquid extraction in an ethanol solvent using a Soxhlet extractor for 6 hours to remove unreacted material, and the remaining solid was dried under a vacuum.

Figure 6:
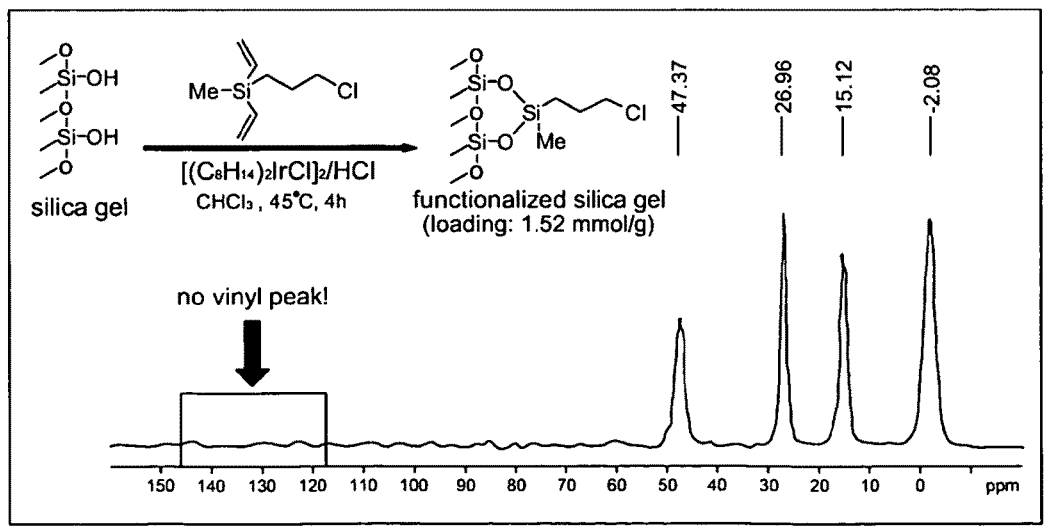
FIG. 6 is a photograph of solid $^{13}C$ CP-MAS NMR taken after allowing 3-chloropropylmethyldivinylsilane to react with amorphous silica at 45□ in a chloroform solvent using $[Ir(C_8H_{14})_2Cl]_2$ and HCl as catalysts.

The solid state NMR for Example 55 is shown in FIG. 6. As can be seen in FIG. 6, it is found that all vinyl groups are disappeared, and 3-chloropropylmethylsilyl group is covalently bonded to the amouphous silica. The loading rate from elemental analysis was found to be 1.52 mmol/g.

Example 56

[Reaction Scheme 20]

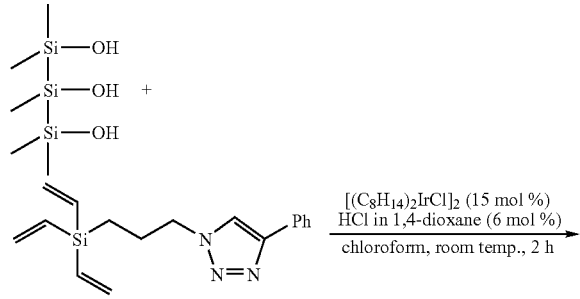

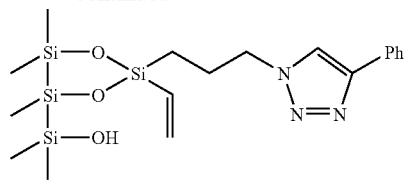

As shown in Reaction Scheme 20 above, in a 1 mL V-vial, 443 mg (1.5 mmol) of 4-phenyl-1-(3-trivinylsilanylpropyl)-1H-[1,2,3]triazole prepared in Reaction Scheme 9, 200 mg of amorphous silica, and 20 mg (1.5 mol %) of [Ir(C$_8$H$_{14}$)$_2$Cl]$_2$ were dissolved in 400 mg of chloroform. After addition of 6 mol % of 4 M HCl in 1,4-dioxane to this solution, the reaction mixture was stirred at room temperature for 2 hours.

After the reaction, the silica solid was placed in a cellulose thimble and subjected to solid-liquid extraction in an methanol solvent using a Soxhlet extractor for 6 hours to remove unreacted material, and the remaining solid was dried under a vacuum.

The results of elemental analysis showed that the weight percentage of carbon was 8.15 wt %, and the weight percentage of nitrogen was 2.13 wt %. Based on the weight percentage of carbon and nitrogen, the loading rate of organic substance onto the silica was calculated as follows. First, 0.0213 g was divided by the molecular weight of nitrogen (14.007 g/mol) and then divided by 3, which is the number of nitrogens impregnated to the amorphous silica. As a result, it was found that 0.507 mmol of the starting material per g of the solid silica was bonded to the surface of the solid silica surface throughout the reaction. The loading rate of organic substance onto the silica was calculated as follows by assumption of the use of 1, 2, or 3 vinyl groups during the reaction, respectively. one vinyl group: (8.15%/100/12 (g/mol)/15 (molecule/number of carbon)*1000 (mg/g)= 0.453 mmol/g; two vinyl groups: (8.15%/100/12 (g/mol)/13 (molecule/number of carbon)*1000 (mg/g)=0.522 mmol/g; three vinyl groups: (8.15%/100/12 (g/mol)/11 (molecule/number of carbon)*1000 (mg/g)=0.617 mmol/g Since the assumpted loading rate of using two vinyl group is closely matched with experimental loading rate, it could be concluded that two vinyl groups must be used in the reaction of amorphous silica and 4-phenyl-1-(3-trivinylsilanylpropyl)-1H-[1,2,3]triazole. From this observation, it can be generalized by that only two vinyl groups in trivinylsilane derivatives were regarded as to be used in this type of reaction.

Example 57

Synthesis of Dodecylmethyldivinylsilane

[Reaction Scheme 21]

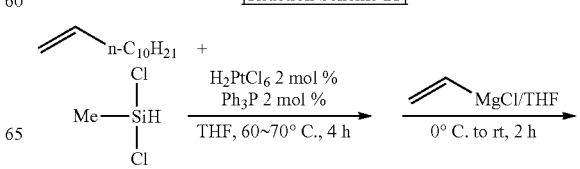

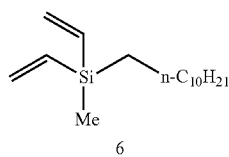

6

As shown in Reaction Scheme 21, the reaction was carried out in the same manner as the reaction for preparing the compound 5 in Reaction Scheme 7, except that dichloromethylsilane (2.7 g, 23.17 mmol) was used in place of chlorodimethylsilane, and 2.7 g (58% yield) of pure dodecylmethyldivinylsilane (6) was obtained.

6: $^1$H NMR (250 MHz, CDCl$_3$) ($\delta$) 6.32-5.55 (m, 6H), 1.37 (s, 20H), 0.99 (t, J=6.5 Hz, 3H), 0.75 (t, J=7.6 Hz, 2H), 0.27 (s, 1H); $^{13}$C NMR (62.9 MHz, CDCl$_3$)($\delta$) 137.3, 132.8, 33.8, 32.1, 29.9, 29.8, 29.6, 24.0, 23.0, 14.3, 14.2, −5.18. IR spectrum (neat) 3043, 2925, 2855, 1589, 1466, 1405, 1250, 1008, 948, 796, 739 cm$^{-1}$. Anal. Calcd for C$_{17}$H$_{34}$Si: C, 76.61; H, 12.86; found: C, 75.8; H, 12.86 HR-MS (CI): m/z calcd for C$_{17}$H$_{35}$Si [M]+=268.2510 found: 267.2508.

Example 58

Synthesis of Dodecyltrivinylsilane

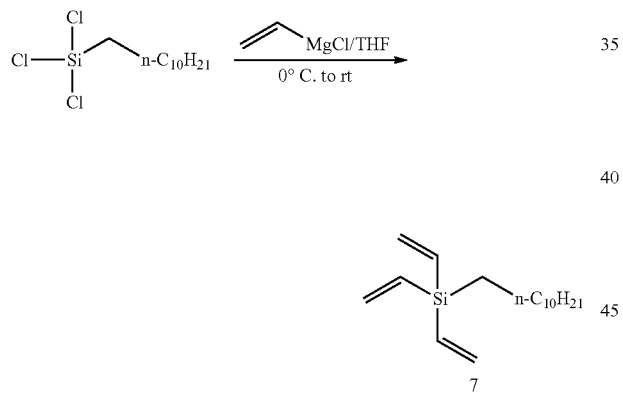

7

As shown in Reaction Scheme 22 above, 3.0 g (9.87 mmol) of dodecyltrimethylchlorosilane was dissolved in 33 ml of THF, to which 25 ml of 1.6 M vinylmagnesium chloride was added. The solution was then stirred at room temperature for 4 hours. After the reaction, the organic layer was extracted with NH$_4$Cl aqueous solution and ether, and washed with saturated aqueous NaCl solution. The washed organic layer was dried with anhydrous MgSO$_4$, and then filtered through celite to remove MgSO$_4$. After evaporating the solvent, the residue was purified by column chromatography (n-Hex: EA=10:1, Rf=0.73) to give 2.2 g (72% yield) of pure dodecyltrivinylsilane (7).

7: $^1$H NMR (250 MHz, CDCl$_3$) ($\delta$) 6.22-5.71 (m, 9H), 1.26 (s, 20H), 0.88 (t, J=6.5 Hz, 3H), 0.74 (t, J=7.7 Hz, 2H); $^{13}$C NMR (62.9 MHz, CDCl$_3$) ($\delta$) 135.2, 134.4, 33.8, 32.2, 29.9, 29.8, 29.6, 29.5, 24.0, 23.0, 14.4, 13.0. IR spectrum (neat) 3048, 2921, 2851, 1589, 1462, 1401, 1005, 952, 756, 719 cm$^{-1}$. Anal. Calcd for C$_{18}$H$_{34}$Si: C, 77.61; H, 12.30; found: C, 77.06; H, 12.29 HR-MS (CI): m/z calcd for C$_{18}$H$_{35}$Si [M]+= 279.2509 found: 279.2508

Example 59~64

The Reactions of Dodecylvinylsilane Derivatives with Amorphous Silica

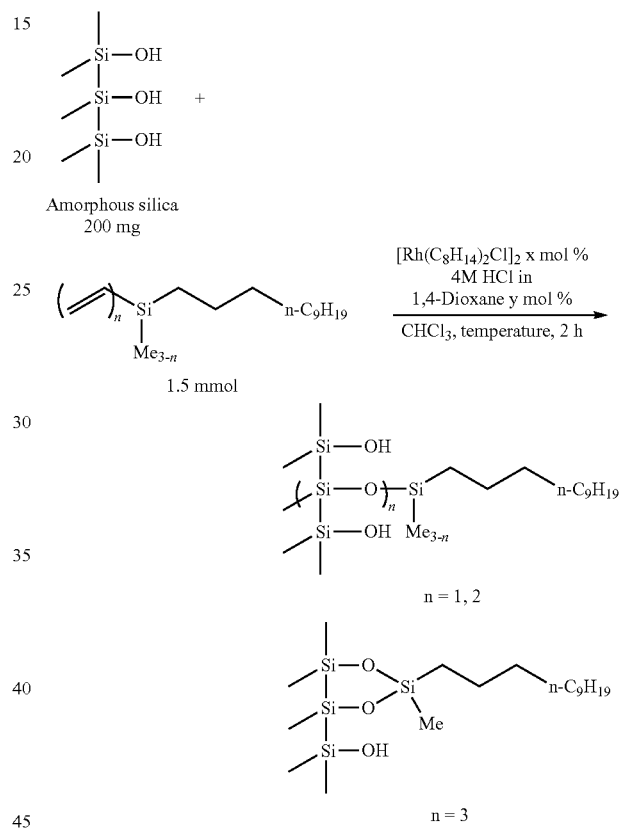

As shown in Reaction Scheme 23 above, in a 1 mL V-vial, 1.5 mmol of dodecyldimethylvinylsilane (prepared from the Reaction Scheme 21), 200 mg of amorphous silica and 1.5 mol % of [Rh(C$_8$H$_{14}$)$_2$Cl]$_2$ were dissolved in 400 mg of chloroform. After addition of 3 mol % of 4 M HCl in 1,4-dioxane to this solution, the reaction mixture was stirred at room temperature for 2 hours. After the reaction, the silica solid was placed in a cellulose thimble and subjected to solid-liquid extraction in an ethanol solvent using a Soxhlet extractor for 6 hours to remove unreacted material, and the remaining solid was dried in a vacuum, followed by analysis for elemental composition (carbon, nitrogen and hydrogen). The loading rate from elemental analysis was found to be 0.529 mmol/g. (see Example 59, Table 9 below)

The procedure of Example 59 above was repeated, except that dodecylmethyldivinylsilane was used in place of dodecylmethyldivinylsilane. The loading rate from elemental analysis was found to be 0.788 mmol/g. (see Example 60, Table 9 below)

The procedure of Example 59 above was repeated, except that dodecyltrivinylsilane was used in place of dodecylmethyldivinylsilane. The loading rate from elemental analysis was found to be 0.659 mmol/g. (see Example 61, Table 9 below)

The procedure of Example 59 above was repeated, except that the reaction temperature increased to 40° C. The loading rate from elemental analysis was found to be 0.630 mmol/g. (see Example 62, Table 9 below)

The procedure of Example 60 above was repeated, except that the reaction temperature increased to 40° C. The loading rate from elemental analysis was found to be 0.712 mmol/g. (see Example 63, Table 9 below)

The procedure of Example 61 above was repeated, except that the reaction temperature increased to 40° C. The loading rate from elemental analysis was found to be 0.889 mmol/g. (see Example 64, Table 9 below)

TABLE 9

The reactions of amorphous silica with dodecylvinylsilanes at different reaction temperature

| Example | product | reaction temperature (° C.) | reaction time (h) | amount of catalyst ($[(C_8H_{14})_2RhCl]_2$/HCl) | amorphous silica (mg) | loading rate (mmol/g) |
| --- | --- | --- | --- | --- | --- | --- |
| Example 59 | (structure) | room temperature | 2 | 1.5 mol %/3 mol % | 200 | 0.529 |
| Example 60 | (structure) | | | | | 0.788 |
| Example 61 | (structure) | | | | | 0.659 |
| Example 62 | (structure) | 40 | | | | 0.630 |
| Example 63 | (structure) | | | | | 0.712 |
| Example 64 | (structure) | | | | | 0.899 |

As shown in Table 9, the reactions of amorphous silica with dodecylvinylsilane were carried out at 40° C. as well as room temperature. According to the results of experiments at 40° C., the loading rate could be found to increase by the increment of number of vinyl groups.

Example 65~72

In order to introduce various organic groups into solid silica, vinylsilane derivatives having various functional groups were synthesized in the following manner.

Example 65

Synthesis of 3-acetoxypropyltrivinylsilane

[Reaction Scheme 24]

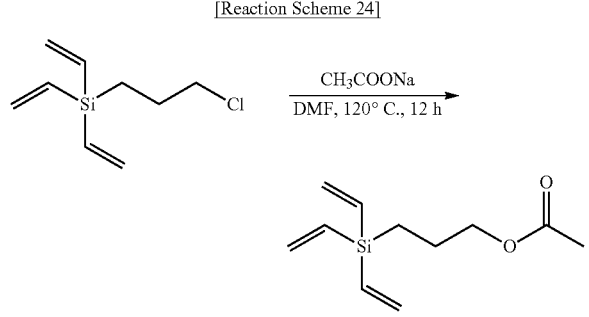

As shown in Reaction Scheme 24, 3-chloropropyltrivinylsilane (1.0 g, 5.35 mmol) and sodium acetate (0.87 g, 10.7 mmol) were dissolved in 17 mL of dimethylformamide (DMF), and the reaction mixture was heated at 120° C. for 12 hours. After the reaction, the organic layer was separated after addition of distilled water and ether. The organic layer was dried over MgSO$_4$, concentrated by evaporation of solvent, and the resulting residue was purified by column chromatography (n-Hex: EA=10:1, Rf=0.4) to give 855 mg (76% yield) of pure 3-acetoxypropyltrivinylsilane.

1H NMR (250 MHz, CDCl$_3$) (ppm) 6.16-5.73 (m, 9H), 4.05-4.00 (t, J=6.89 Hz, 2H), 2.04 (s, 3H), 1.70-1.65 (m, 2H), 0.79-0.72 (m, 2H); $^{13}$C NMR (62.9 MHz, CDCl$_3$) (ppm) 171.4, 135.1, 134.3, 67.1, 23.17, 21.3, 8.89. IR spectrum (neat) 3048, 2938, 1740, 1234 cm$^{-1}$.

Example 66

Synthesis of 3-cyanopropyltrivinylsilane

[Reaction Scheme 25]

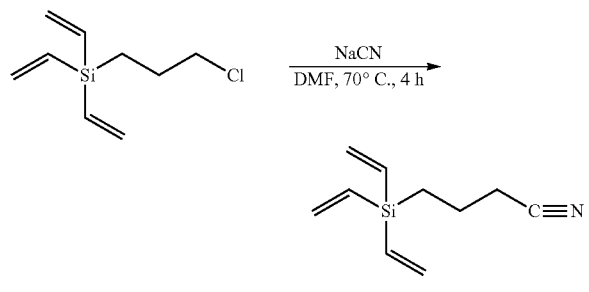

Compound 3-chloropropyltrivinylsilane (1000 mg, 5.35 mmol) and sodium cyanide (525 mg, 10.70 mmol) were dissolved in 18 ml of dimethylformamide, and the mixture was heated at 70° C. for 4 hours. After the reaction, the organic layer was extracted after addition of distilled water and ether, and then purified by column chromatography (n-Hex:EA=10:1, Rf=0.42), to give 818 mg (86% yield) of pure 3-cyanopropyltrivinylsilane.

$^1$H NMR (250 MHz, CDCl$_3$) (ppm) 6.19-5.70 (m, 9H), 2.37-2.32 (t, J=6.96 Hz 2H), 1.76-1.63 (m, 2H), 0.91-0.84 (m, 2H); $^{13}$C NMR (62.9 MHz, CDCl$_3$) (ppm) 135.3, 133.5, 119.7, 20.6, 20.3, 12.3; IR spectrum (neat) 3052, 2942, 2239, 1593, 1405, 1005, 960, 727 cm$^{-1}$.

Example 67

Synthesis of 4-trivinylsilanylbutylaldehyde

[Reaction Scheme 26]

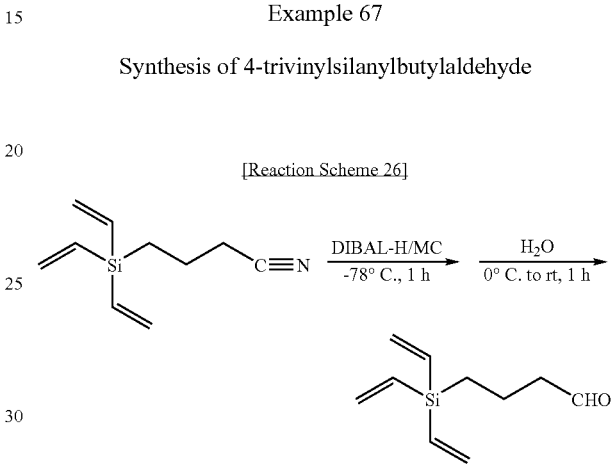

As shown in Reaction Scheme 26 above, 3-cyanopropyltrivinylsilane (1.03 g, 5.8 mmol) was dissolved in methylene chloride, and the solution was cooled to a temperature of −78°. Then, 6.4 mL of a solution of 1.0 M diisobutylaluminum hydride (DIBAL-H) in methylene chloride was slowly added thereto. After elevating the temperature of the solution to −40°, the solution of mixture was stirred for one additional hour. To the stirred solution, silica and distilled water were added, and the solution of mixture was stirred at 0° for 1 hour and then dried with anhydrous K$_2$CO$_3$ and MgSO$_4$. The dried mixture was filtered through celite to remove K$_2$CO$_3$ and MgSO$_4$. After removing the solvent, 743 mg (72% yield) of pure 4-trivinylsilanylbutylaldehyde was obtained.

1H NMR (250 MHz, CDCl$_3$) (ppm) 9.76-9.74 (t, J=1.7 Hz, 1H) 6.22-5.71 (m, 9H), 2.51-2.45 (m, 2H), 1.75-1.68 (m, 2H), 0.81-0.74 (m, 2H); $^{13}$C NMR (62.9 MHz, CDCl$_3$) (ppm) 203.0, 135.1, 134.3, 47.4, 16.8, 13.0.

Example 68

Synthesis of 1-(3-dimethylvinylsilanyl)propyl-1-hydro-[1,2,3]triazolylmethanol

[Reaction Scheme 27]

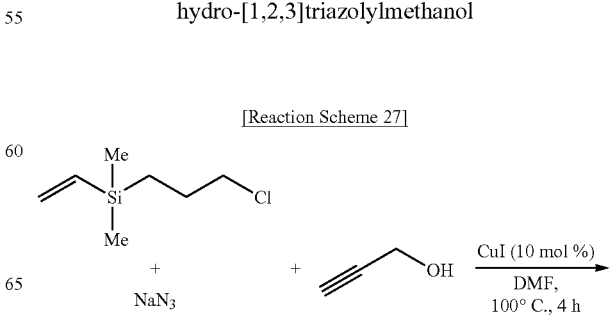

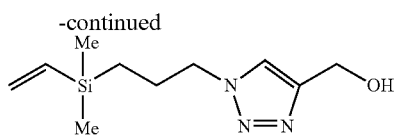

As shown in Reaction Scheme 27 above, 3-chloropropyl dimethylvinylsilane (325.4 mg, 2.0 mmol), propargyl alcohol (117.7 mg, 2.1 mmol), and sodium azide (136.5 mg, 2.1 mmol) were dissolved in 2 ml of N,N'-dimethylforamide (DMF). To this solution, copper iodide (38.1 mg, 0.2 mmol) was added, and the resulting mixture was stirred at 100° C. for 4 hours. After the reaction, the organic layer was extracted with methylene chloride and saturated aqueous NaCl solution. The organic layer was dried over anhydrous MgSO$_4$ filtered through celite to remove MgSO$_4$, and the resulting residue was purified by column chromatography (n-Hex: EA=10:1, Rf=0.31) to give 315 mg (70% yield) of pure 1-(3-dimethylvinylsilanyl)propyl-1-hydro-[1,2,3]triazolylmethanol.

$^1$H NMR (250 MHz, CDCl$_3$) (ppm) 7.60 (s, 1H) 6.17-5.92 (m, 3H) 4.94 (s, 6H), 4.77 (s, 2H), 4.34-4.28 (t, 2H), 1.95-1.82 (m, 2H), 0.59-0.52 (m, 2H) 0.07 (s, 6H). IR spectrum (neat) 3354, 3047, 2950, 1667, 1405, 1246, 1049, 837, 698 cm$^{-1}$; Anal. Calcd for C$_{10}$H$_{19}$N$_3$OSi: C, 53.29; H, 8.50; N, 18.65; found: C, 50.09; H, 8.22; N, 17.83; HR-MS (TOF) calcd for C$_{10}$H$_{19}$N$_3$OSi [M+Na]$^+$=248.1195 found: 248.1192.

Example 69

Synthesis of 1-(3-dimethylvinylsilanyl)propyl-4-phenyl-1-hydro-[1,2,3]triazole

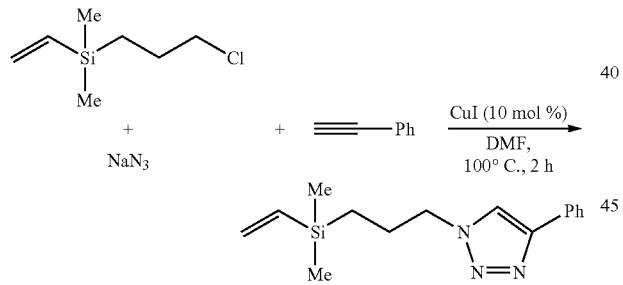

[Reaction Scheme 28]

As shown in Reaction Scheme 28, 3-chloropropyldimethylvinylsilane (325.4 mg, 2.0 mmol), phenyl acetylene (214.5 mg, 2.1 mmol), and sodium azide (136.5 mg, 2.1 mmol) were dissolved in 2 ml of N,N'-dimethylforamide (DMF). To this mixture, copper iodide (38 mg, 0.2 mmol) was added, and the resulting mixture was stirred at 100° C. for 2 hours. After the reaction, the organic layer was extracted with methylene chloride and aqueous saturated NaCl solution. The organic layer was dried with anhydrous MgSO$_4$ and filtered through celite to remove MgSO$_4$. After evaporating the solvent, the residue was purified by column chromatography (n-Hex: EA=5:1, Rf=0.23) to give 445 mg (82% yield) of pure 1-(3-dimethylvinylsilanyl) propyl-4-phenyl-1-hydro-[1,2,3]triazole.

$^1$H NMR (250 MHz, CDCl$_3$) (ppm) 8.02-7.44 (m, 5H) 6.34-5.79 (m, 3H) 4.55-4.49 (t, J=7.2 Hz, 2H), 2.16-2.03 (m, 2H), 0.78-0.71 (m, 2H) 0.24 (s, 6H); $^{13}$C NMR (62.9 MHz, CDCl$_3$) (ppm) 147.5, 137.9, 132.3, 130.7, 128.7, 127.9, 125.6, 119.6, 53.2, 25.3, 25.2, 12.7, −3.6. IR spectrum (neat) 2949, 1609, 1241, 833, 764, 690 cm$^{-1}$; Anal. Calcd for C$_{15}$H$_{21}$N$_3$Si: C, 66.37; H, 7.80; N, 15.48 found: C, 66.30H, 7.36; N, 15.51.

Example 70

Synthesis of 1-(3-dimethylvinylsilanyl)propyl-4-ferrocenyl-1-hydro-[1,2,3]triazole

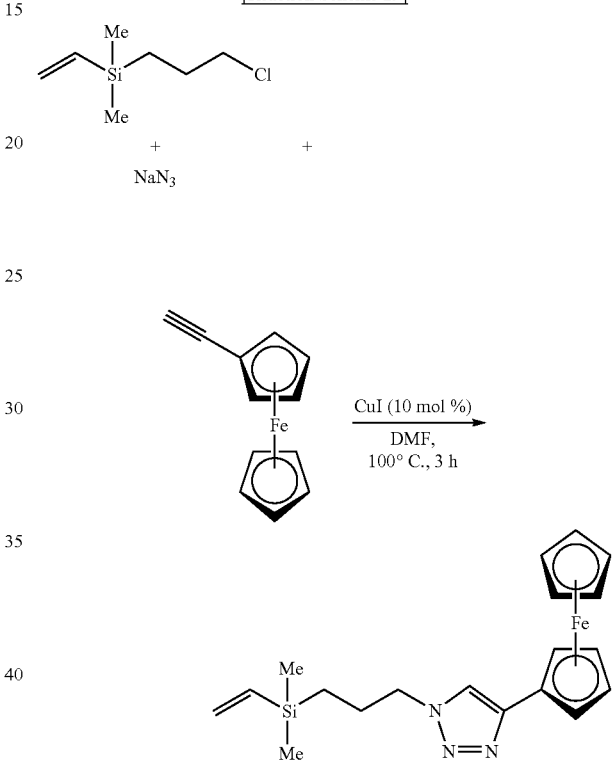

[Reaction Scheme 29]

As shown in Reaction Scheme 29, 3-chloropropyldimethylvinylsilane (325.4 mg, 2.0 mmol), ethynylferrocene (179 mg, 1.0 mmol), and sodium azide (71.5 mg, 1.1 mmol) were dissolved in 1.5 ml of N,N'-dimethylforamide (DMF). To this mixture, copper iodide (19.0 mg, 0.1 mmol) was added, and the resulting mixture was stirred at 100° C. for 3 hours. After the reaction, the organic layer was extracted with methylene chloride and aqueous saturated NaCl solution. The organic layer was dried over anhydrous MgSO$_4$ and filtered through celite to remove MgSO$_4$. After evaporating the solvent, the residue was purified by column chromatography (n-Hex: EA=5:1, Rf=0.34) to give 261 mg (69% yield) of pure 1-(3-dimethylvinylsilanyl)propyl-4-ferrocenyl-1-hydro-[1,2,3] triazole.

$^1$H NMR (250 MHz, CDCl$_3$) (ppm) 7.44 (s, 1H) 6.18-5.62 (m, 3H) 4.72 (s, 2H), 4.35-4.07 (m, 9H), 1.97-1.85 (m, 2H) 0.59-0.52 (m, 2H) 0.07 (s, 6H); $^{13}$C NMR (62.9 MHz, CDCl$_3$) (ppm) 146.8, 138.2, 132.6, 118.9, 69.7, 68.8, 66.8, 53.3, 25.4, 12.6, −3.4; IR spectrum (neat) 3120, 3045, 2943, 2894, 1630, 1591, 1463, 1433, 1404, 1246, 1217, 1102, 1046, 1000, 951 cm$^{-1}$; Anal. Calcd for C$_{19}$H$_{25}$FeN$_3$Si: C, 60.16; H, 6.64; N, 11.08 found: C, 58.98H, 6.25; N, 11.14 HR-MS: m/z calcd for C₁₉H₂₅FeN₃Si [M+H]⁺=379.1167 found: 380.1175

Example 71

Synthesis of 3-cyanopropyldimethylvinylsilane

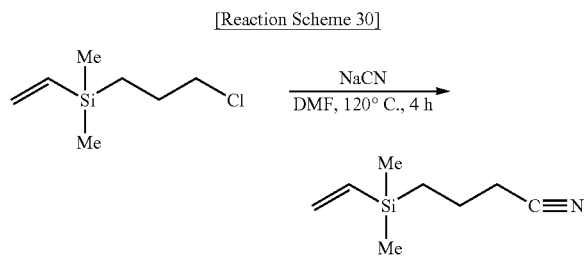

[Reaction Scheme 30]

As shown in Reaction Scheme 30, 3-chloropropyltrivinylsilane (2.0 g, 12.29 mmol) and sodium cyanide (1.2 g, 24.6 mmol) were dissolved in 40 ml of N,N'-dimethylformamide (DMF). The reaction mixture was heated at 120° C. for 4 hours. After cooling down to the room temperature, the organic layer was extracted with distilled water and ether, and evaporated in vacuum. The residue was purified by column chromatography (n-Hex: EA=10:1, Rf=0.37) to give 1.60 g (85% yield) of pure 3-cyanopropyldimethylvinylsilane.

$^1$H NMR (250 MHz, CDCl₃) (ppm) 6.39-5.66 (m, 3H), 2.40-2.35 (t, J=7.0 Hz 2H), 1.72-1.63 (m, 2H), 0.78-0.73 (m, 2H), 0.095 (s, 6H); $^{13}$C NMR (62.9 MHz, CDCl₃) (ppm) 137.9, 132.5, 119.8, 20.8, 20.6, 15.1, −3.59; IR spectrum (neat) 3044, 2950, 2243, 1593, 1405, 1246, 1009, 952, 837 cm⁻¹.

Example 72

Synthesis of 4-dimethylvinylsilanylbutyraldehyde

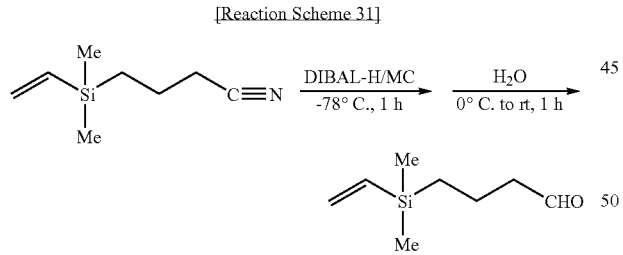

[Reaction Scheme 31]

As shown in Reaction Scheme 31, 3-cyanopropyldimethylvinylsilane (1.03 g, 5.8 mmol) dissolved in methylene chloride was cooled down to −78°. To this solution, 7.8 mL of a solution of 1.0 M diisobutylaluminum hydride (DIBAL-H) in methylene chloride was slowly added. After completing the addition, the temperature of the solution was elevated to −40°, and was continually stirred for one additional hour. To this solution, silica and distilled water were added, and the solution of mixture was stirred at 0° for 1 hour and then dried over anhydrous K₂CO₃ and MgSO₄. After removing the solvent, 634 mg (70% yield) of pure 4-dimethylvinylsilanylbutylaldehyde was obtained.

$^1$H NMR (250 MHz, CDCl₃) (ppm) 10.1 (s, 1H) 6.44-5.66 (m, 3H), 2.52-2.45 (m, 2H), 1.72-1.62 (m, 2H), 0.83 (s, 6H); $^{13}$C NMR (62.9 MHz, CDCl₃) (ppm) 203.0, 138.7, 132.1, 47.5, 16.9, 15.4, −3.4; IR spectrum (neat) 3048, 2954, 2709, 1724, 1405, 1246, 1005, 837, 772 cm⁻¹.

Example 73

Reactions of Vinylsilane Derivatives Having Various Functional Groups and Amorphous Silica

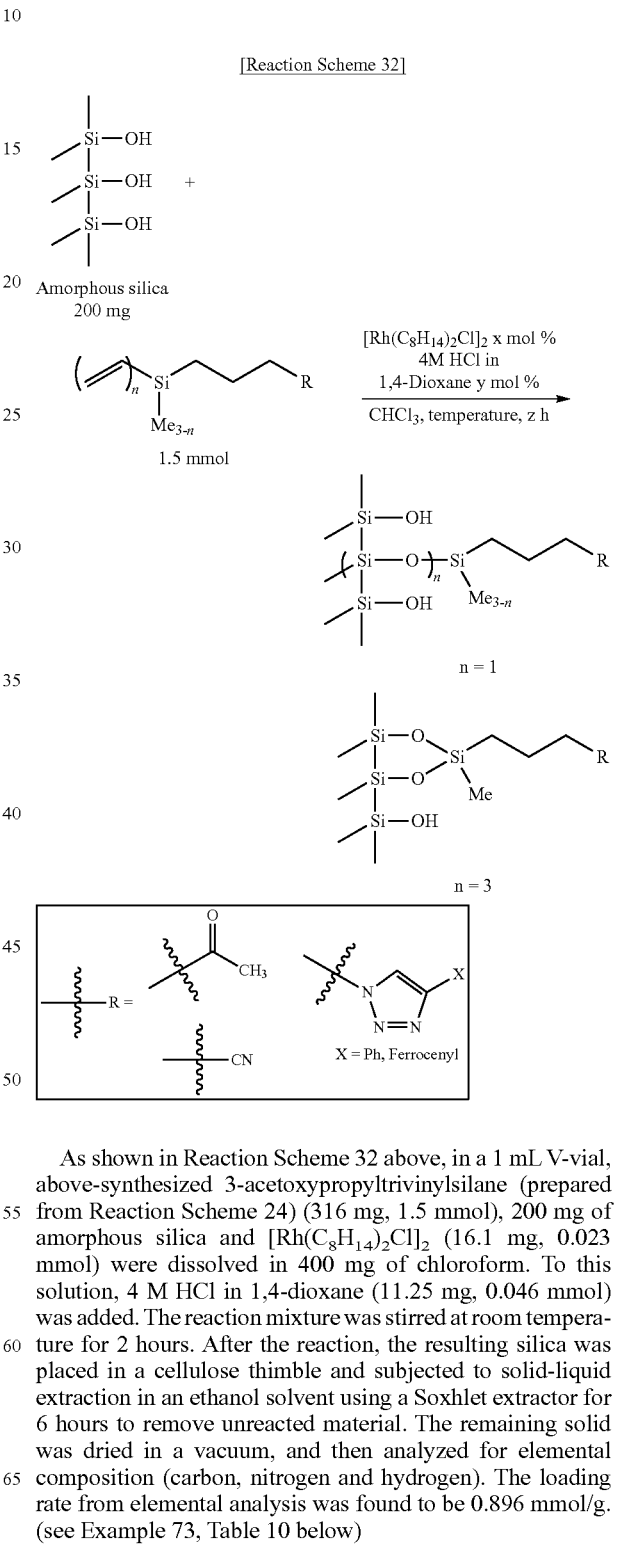

[Reaction Scheme 32]

As shown in Reaction Scheme 32 above, in a 1 mL V-vial, above-synthesized 3-acetoxypropyltrivinylsilane (prepared from Reaction Scheme 24) (316 mg, 1.5 mmol), 200 mg of amorphous silica and [Rh(C₈H₁₄)₂Cl]₂ (16.1 mg, 0.023 mmol) were dissolved in 400 mg of chloroform. To this solution, 4 M HCl in 1,4-dioxane (11.25 mg, 0.046 mmol) was added. The reaction mixture was stirred at room temperature for 2 hours. After the reaction, the resulting silica was placed in a cellulose thimble and subjected to solid-liquid extraction in an ethanol solvent using a Soxhlet extractor for 6 hours to remove unreacted material. The remaining solid was dried in a vacuum, and then analyzed for elemental composition (carbon, nitrogen and hydrogen). The loading rate from elemental analysis was found to be 0.896 mmol/g. (see Example 73, Table 10 below)

Table 10 shows the results of the reactions of functionalized vinylsilane derivatives with amorphous silica in the presence of Rh(I) catalyst and acid catalyst through the same manner as the reaction procedure of Reaction Scheme 32. Depending on the vinylsilane derivatives, different reaction conditions such as amounts of rhodium catalyst and acid catalyst, temperature and reaction time were applied. The loading rate of the silica sample obtained by the reaction with 3-cyanopropyltrivinylsilane was found to be 0.255 mmol/g (Example 74, See Table 10.), and the loading rate of the silica samples obtained by the reactions with 1-(3-dimethylvinyl-silanyl)propyl-4-phenyl-1-hydro-[1,2,3]triazole, ferrocene-vinylsilane derivative, 3-acetoxypropyldimethylvinylsilane and 3-cyanopropyldimethylvinylsilane were found to be 0.492, 0.624, 0.924, 0.384 mmol/g, respectively (Example 75~78, See Table 10.).

TABLE 10

The reactions of amorphous silica with functionalized vinylsilane derivatives

| Example | product | reaction temperature (° C.) | reaction time (h) | amount of catalyst ([($C_8H_{14}$)$_2$RhCl]$_2$/HCl) | amorphous silica (mg) | loading rate (mmol/g) |
|---|---|---|---|---|---|---|
| Example 73 | | room temperature | 2 | 1.5 mol %/3 mol % | 200 | 0.896 |
| Example 74 | | room temperature | 2 | 1.5 mol %/3 mol % | | 0.255 |
| Example 75 | | room temperature | 3 | 2.5 mol %/5 mol % | | 0.472 |
| Example 76 | | 40° C. | 20 | 1.5 mol %/3 mol % | | 0.624 |
| Example 77 | | room temperature | 2 | 1.5 mol %/9 mol % | | 0.924 |
| Example 78 | | room temperature | 2 | 1.5 mol %/9 mol % | | 0.384 |

Example 79~96

The Reaction of ITO Glass with Vinylsilane Derivative

Example 79

Surface Modification of ITO Glass by the Treatment of Piranha Solution

Figure 7:
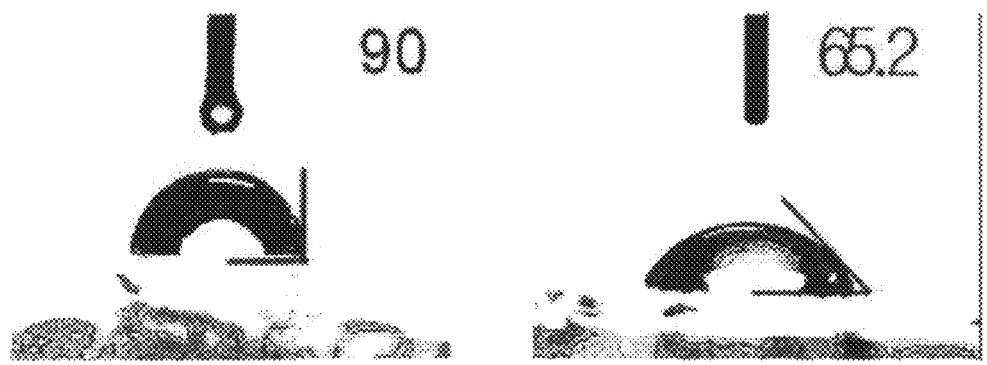
FIG. 7 is a photograph showing contact angle test results for ITO glass before and after treating the ITO glass with a piranha solution.

In order to immobilize the above-synthesized various vinylsilane derivatives to indium tin oxide (ITO) glass which can be mainly used in electronic sensor or semiconductor applications, an activation step of generating —OH groups on the ITO glass surface should be carried out by treating ITO's surface with Piranha solution. The Piranha solution was prepared by slowly mixing $H_2SO_4$ and $H_2O_2$ in a 3:1 ratio. The ITO glass was immersed in the Piranha solution for about 30 minutes, and then washed with ethanol and distilled water, thus making many hydroxy groups on the ITO glass surface. As a result of this treatment, the glass surface became hydrophilic due to many hydroxyl groups. As shown in FIG. 7, a water drop was allowed to fall on the glass surface, and the contact angle between the glass surface and the water drop was measured as 65.2°. The contact angle before the treatment of Piranha solution was measured as 900. (See Table 11.)

Example 80

[Reaction Scheme 33]

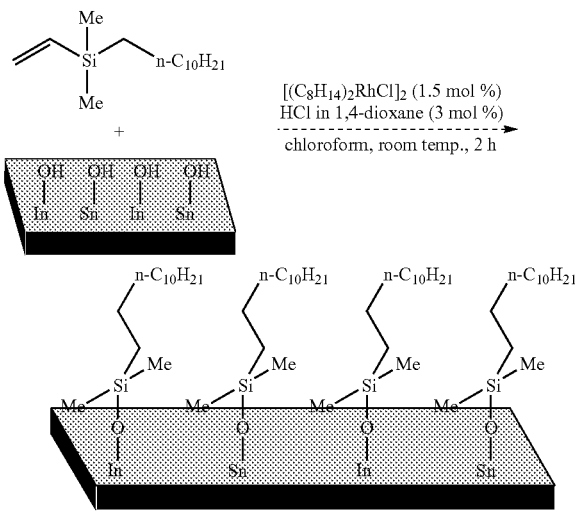

Figure 8:
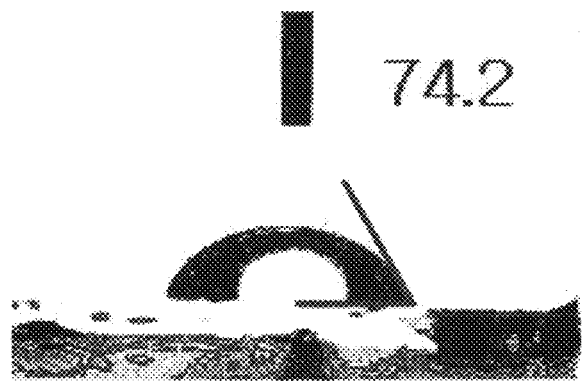
FIG. 8 is a photograph showing the results of a contact angle test conducted after allowing dodecyl dimethylvinylsilane to react with ITO glass at room temperature in a chloroform solvent using 1.5 mol % of $[Rh(C_8H_{14})_2Cl]_2$ and 3 mol % of HCl as catalysts.

As shown in Reaction Scheme 33 above, 382 mg (1.5 mmol) of dodecyldimethylvinylsilane (5 in Reaction Scheme 7), and 16.1 mg (0.023 mmol) of $[Rh(C_8H_{14})_2Cl]_2$ were dissolved in 400 mg of chloroform, and then 11.25 mg (0.046 mmol) of 4.0 M HCl in 1,4-dioxane was added. The solution was allowed to react with ITO glass for 2 hours. After the reaction, ITO glass was washed with ethanol and distilled water. This dodecyldimethylsilyl group-immobilized ITO glass showed a contact angle of 74.2°, as shown in FIG. 8. (Example 80, See Table 11.)

Example 81

[Reaction Scheme 34]

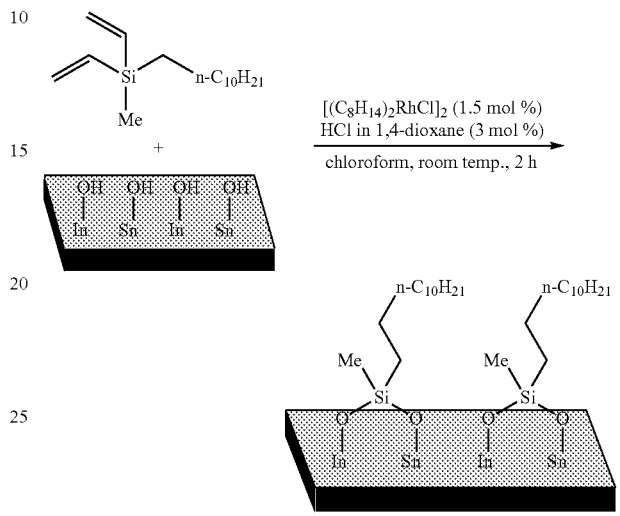

Figure 9:
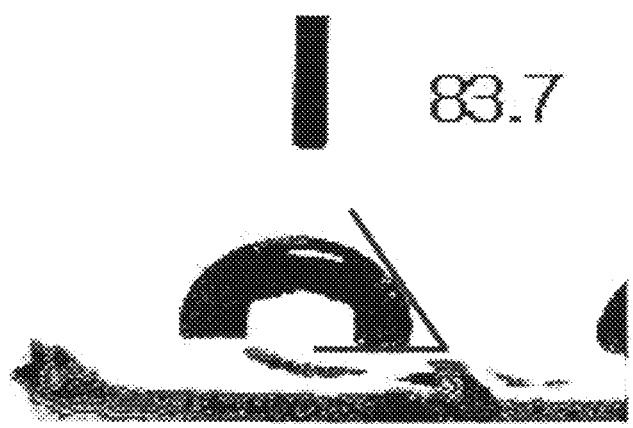
FIG. 9 is a photograph showing the results of a contact angle test conducted after allowing dodecyl methyldivinylsilane to react with ITO glass at room temperature in a chloroform solvent using 1.5 mol % of $[Rh(C_8H_{14})_2Cl]_2$ and 3 mol % of HCl as catalysts.

As shown in Reaction Scheme 34, the reaction was carried out in the same manner as in the Reaction Scheme 80, except that dodecylmethyldivinylsilane (6 of Reaction Scheme 21, 400 mg, 1.5 mmol) was used instead of dodecyldimethylvinylsilane. As a result, ITO glass from the reaction with dodecylmethyldivinylsilane (6) showed a contact angle of 83.7, as shown in FIG. 9. (Example 81, See Table 11.)

Example 82

[Reaction Scheme 35]

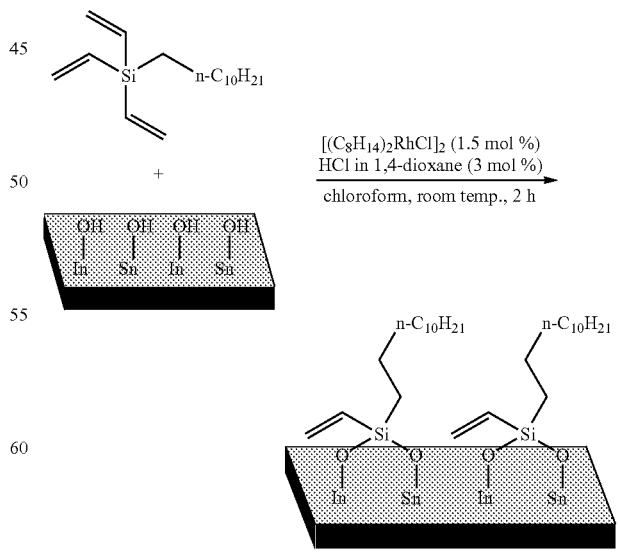

Figure 10:
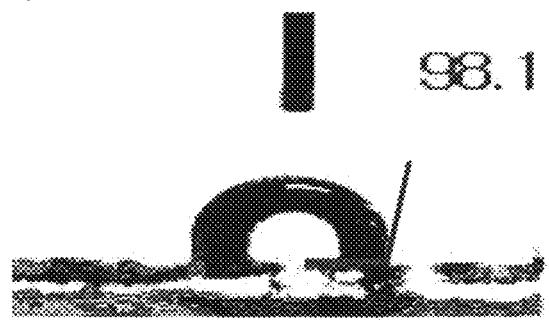
FIG. 10 is a photograph showing the results of a contact angle test conducted after allowing dodecyl trivinylsilane to react with ITO glass at room temperature in a chloroform solvent using 1.5 mol % of $[Rh(C_8H_{14})_2Cl]_2$ and 3 mol % of HCl as catalysts.

As shown in Reaction Scheme 35, the reaction was carried out in the same manner as in the Reaction Scheme 80, except that dodecylmethyldivinylsilane (7 of Reaction Scheme 22, (417.8 mg, 1.5 mmol)) was used instead of dodecyldimethylvinylsilane. As a result, ITO glass from the reaction with dodecylmethyldivinylsilane (7) showed a contact angle of 98.1, as shown in FIG. 10. (Example 82, See Table 11.)

Example 83~86

The ITO glass for immobilization was prepared by treatment of Piranha solution as in Example 79, and the contact angle of the resulting ITO glass was measured as 59.1° (Example 83, See Table 11.).

The reaction was carried out in the same manner as in the Reaction Scheme 80, except that 9 mol % of HCl was used. As a result, contact angle was measured as 65.8° (Example 84, See Table 11.)

The reaction was carried out in the same manner as in the Reaction Scheme 81, except that 9 mol % of HCl was used. As a result, contact angle was measured as 67.2° (Example 85, See Table 11.)

The reaction was carried out in the same manner as in the Reaction Scheme 82, except that 9 mol % of HCl was used. As a result, contact angle was measured as 77.5° (Example 86, See Table 11.)

was used instead of $[(C_8H_{14})_2RhCl]_2$. As a result, the contact angle of dodecyl group-immobilized ITO glass from divinylsilane was measured as 81.7° (Example 89, See Table 11-ii.)

The reaction was carried out in the same manner as the reaction in Reaction Scheme 82, except that 1.5 mol % of $[(C_8H_{14})_2IrCl]_2$ was used in place of $[(C_8H_{14})_2RhCl]_2$. As a result, the contact angle of dodecyl group-immobilized ITO glass from trivinylsilane was measured as 83.7° (Example 90, See Table 11-iii.)

The reaction was carried out in the same manner as in the Reaction Scheme 88, except that 6 mol % of HCl was used. As a result, the contact angle of dodecyl group-immobilized ITO glass from monovinylsilane was measured as 82.50 (Example 91, See Table 11-iv.)

The reaction was carried out in the same manner as the reaction in Reaction Scheme 89, except that 6 mol % of HCl was used. As a result, the contact angle of dodecyl group-immobilized ITO glass from divinylsilane was measured as 85.4° (Example 92, See Table 11-v.)

The reaction was carried out in the same manner as in the Reaction Scheme 90, except that 6 mol % of HCl was used. As a result, the contact angle of dodecyl group-immobilized ITO glass from trivinylsilane was measured as 90.8° (Example 93, See Table 11-vi.)

TABLE 11

Modification of surface of ITO glass with dodecylvinylsilane

| Contact angle of ITO glass after treatment by piranha solution | Me-Si(Me)-n-C$_{10}$H$_{21}$ | CH$_2$=CH-Si(Me)-n-C$_{10}$H$_{21}$ | (CH$_2$=CH)$_2$Si-n-C$_{10}$H$_{21}$ | (CH$_2$=CH)$_3$Si-n-C$_{10}$H$_{21}$ |
|---|---|---|---|---|
| HCl 3 mol % | 65.2° (Example 79) | 74.2° (Example 80) | 83.7° (Example 81) | 98.1° (Example 82) |
| HCl 9 mol % | 59.1° (Example 83) | 65.8° (Example 84) | 67.2° (Example 85) | 77.5° (Example 86) |

It was observed that contact angle increased along with the increment of the number of vinyl groups due to the formation of a stronger covalent bond from the reaction of each vinyl group and hydroxyl group on the surface of ITO glass to achieve effective surface modification.

Also, these results showed that the proper concentration of HCl in this reaction was 3 mol % of HCl, and any remarkable result for efficiency could not be seen with increasing the concentration of HCl.

Example 87~96

The Reaction of ITO Glass with Dodecylvinylsilane Derivative in the Presence of Ir(I) Catalyst

Figure 11:
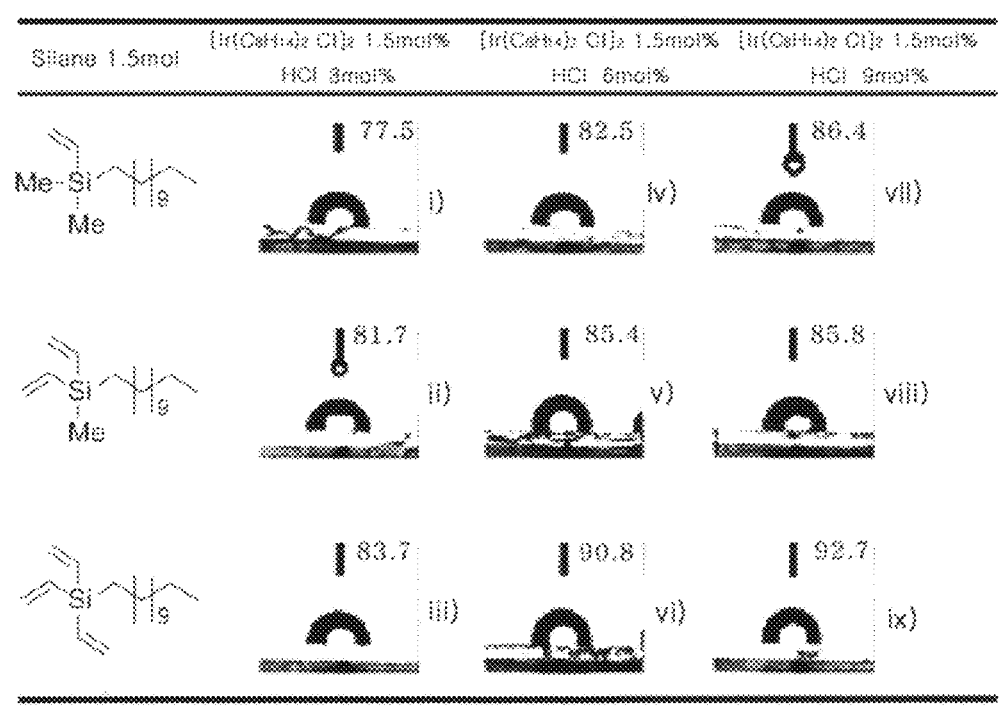
FIG. 11 illustrates photographs showing the results of contact angle tests conducted after allowing dodecyldimethylvinylsilane, dodecylmethyldivinylsilane or dodecyltrivinylsilane to react with ITO glass at room temperature in a chloroform solvent using 1.5 mol % of $[Ir(C_8H_{14})_2Cl]_2$ and 3 mol %, 6 mol % or 6 mol % of HCl as catalysts.

The ITO glass was treated with Piranha solution in the same manner as in Example 79. And the contact angle of the resulting ITO glass was measured as 61.2° (Example 87, See FIG. 11.).

The reaction was carried out in the same manner as in the Reaction Scheme 80, except that 1.5 mol % of $[(C_8H_{14})_2 IrCl]_2$ was used instead of $[(C_8H_{14})_2RhCl]_2$. As a result, the contact angle of dodecyl group-immobilized ITO glass from monovinylsilane was measured as 77.5° (Example 88, See Table 11-i.)

The reaction was carried out in the same manner as in the Reaction Scheme 81, except that 1.5 mol % of $[(C_8H_{14})_2 rCl]_2$ The reaction was carried out in the same manner as in the Reaction Scheme 88, except that 9 mol % of HCl was used. As a result, the contact angle of dodecyl group-immobilized ITO glass from mono-vinylsilane was measured as 86.4° (Example 91, See Table 11-vii.)

The reaction was carried out in the same manner as in the Reaction Scheme 89, except that 9 mol % of HCl was used. As a result, the contact angle of dodecyl group-immobilized ITO glass from Ovinylsilane was measured as 85.8° (Example 92, See Table 11-viii.)

The reaction was carried out in the same manner as in the Reaction Scheme 90, except that 9 mol % of HCl was used. As a result, the contact angle of dodecyl group-immobilized ITO glass from trivinylsilane was measured as 92.7° (Example 93, See Table 11-ix.)

As shown in Example 87-96, Ir(I) catalyst as well as Rh(I) catalyst showed good catalytic activity for the reaction of ITO glass with dodecylvinylsilane derivatives. The above results showed that the contact angle increases as the number of vinyl groups in vinylsilane derivatives increase. Thus, it can be concluded that divinylsilane or trivinylsilane derivatives are more efficient substrate for immobilization than monovinylsilane derivatives. In these reactions, the best results were obtained with catalytic composition of 1.5 mol % of $[(C_8H_{14})_2 IrCl]_2$ and 9 mol % of HCl.

INDUSTRIAL APPLICABILITY

As described above, according to the present invention, alcohol can be effectively silylated even at room temperature by increasing the activity of the reaction using the transition metal catalyst and the acid catalyst. Also, an organic compound can be effectively introduced into solid silica or ITO glass, and thus the present invention is highly effective in introducing natural compounds or thermally sensitive organic functional groups into solid silica or ITO glass. Furthermore, in the present invention, a process for pre-treating the organic-inorganic hybrid glass is not required, and the reaction between the silane compound, having vinyl or a vinyl derivative, and the organic-inorganic hybrid glass can be performed after an organic functional group is introduced into the silane compound. Accordingly, the present invention gives a high reaction yield and is highly useful in the chemical industry.

The invention claimed is:

1. A method for modifying the surface of an inorganic glass comprising the steps of:
   1) purifying a silane compound represented by Formula 1, having vinyl or a vinyl derivative; and
   2) mixing an organic-inorganic hybrid glass with the purified compound, a transition metal catalyst, an acid catalyst and an organic solvent:

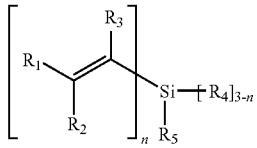

[Formula 1]

wherein $R_1$ to $R_4$ are each independently optionally substituted H or an optionally substituted alkyl group, $R_5$ is at least one selected from the group consisting of an optionally substituted alkyl or cycloalkyl group, an optionally substituted aromatic or heteroaromatic group, and optionally substituted halogen, azide, amine, ketone, ether, amide, ester, triazole and isocyanate groups, and n is an integer ranging from 1 to 3.

2. The method for modifying the surface of an inorganic glass according to claim 1, wherein, in said Formula 1, $R_1$ to $R_4$ are each independently optionally substituted H or an optionally substituted $C_1$-$C_{30}$ alkyl group, and $R_5$ is at least one selected from the group consisting of an optionally substituted $C_1$-$C_{30}$ alkyl group, an optionally substituted $C_1$-$C_{30}$ cycloalkyl group, an optionally substituted $C_1$-$C_{30}$ aromatic or $C_1$-$C_{30}$ heteroaromatic ring compound, halogen, azide, amine, ketone, ether, amide, ester, triazole and isocyanate.

3. The method for modifying the surface of an inorganic glass according to claim 1, wherein the inorganic glass is solid silica or ITO glass.

4. The method for modifying the surface of an inorganic glass according to claim 1, wherein the purification in the step 1) is carried out through column chromatography.

5. The method for modifying the surface of an inorganic glass according to claim 1, wherein the step 2) is carried out at 0-45°.

6. The method for modifying the surface of an inorganic glass according to claim 1, wherein the transition metal catalyst is rhodium or iridium.

7. The method for modifying the surface of an inorganic glass according to claim 1, wherein the acid is at least one selected from the group consisting of HCl, HBr and HI.

8. The method of claim 1, wherein the organic solvent is at least one selected from the group consisting of toluene, benzene, methylene chloride, chloroform, THF and dimethylacetamide (DMA).

9. The method for modifying the surface of an inorganic glass according to claim 1, which further comprises, after the step 2), a step of stirring the mixture for a period ranging from 5 minutes to 24 hours.

10. The method for modifying the surface of an inorganic glass according to claim 1, which further comprises, before the step 1) or after the step 2), a step of introducing an organic group into said $R_5$.

11. The method for modifying the surface of an inorganic glass according to claim 10, wherein the organic group is at least one selected from the group consisting of amino acids, proteins, and chiral compounds.

* * * * *